United States Patent [19]

Cook

[11] 3,937,711

[45] Feb. 10, 1976

[54] 4-(CARBOXAMIDOETHYL) PIPERIDINES

[75] Inventor: Barry Cook, Flixton, England

[73] Assignee: Ciba-Geigy Corporation, Ardsley, N.Y.

[22] Filed: Oct. 15, 1973

[21] Appl. No.: 406,527

[52] U.S. Cl.... 260/293.86; 260/45.8 N; 260/240 R; 260/240 K; 260/293.51; 260/293.52; 260/293.56; 260/293.62; 260/293.63; 260/293.64; 260/293.65; 260/293.66; 260/293.73; 260/293.75; 260/293.76; 260/293.77; 260/293.78; 260/293.81; 260/293.82; 260/293.87; 260/293.88

[51] Int. Cl.².................................. C07D 211/32

[58] Field of Search...... 260/293.86, 293.66, 240 K, 260/293.56, 293.62, 293.65, 293.73, 293.75, 293.76, 293.85

[56] References Cited

UNITED STATES PATENTS

| | | | |
|---|---|---|---|
| 3,101,341 | 8/1963 | Cusic et al. | 260/293.86 |
| 3,147,268 | 9/1964 | Meltzer et al. | 260/293.86 |
| 3,705,166 | 12/1972 | Murayama et al. | 260/293.86 |
| 3,828,052 | 8/1974 | Holt et al. | 260/293.86 |

OTHER PUBLICATIONS

JACS, 81:4,666, (1959), Augustine.

*Primary Examiner*—Sherman D. Winters
*Attorney, Agent, or Firm*—Nestor W. Shust

[57] ABSTRACT

New piperidine derivatives and in particular 2-(piperidinyl-4')-ethyl-amines, -ethers and -esters are used as stabilisers for polymers, especially for polyolefines.

8 Claims, No Drawings

4-(CARBOXAMIDOETHYL) PIPERIDINES

The present invention relates to new piperidine derivatives and in particular to new 2-(piperidinyl-4')-ethyl derivatives useful as light stabilisers for polymers.

According to the present invention, there are provided compounds having the formula I

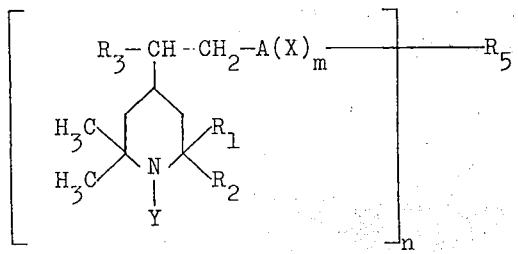

and salts thereof wherein $m$ is 0 or 1; $n$ is 1 or 2; $R_1$ and $R_2$ are the same or different and each is a straight- or branched chain alkyl residue having from 1 to 12 carbon atoms or $R_1$ and $R_2$, together with the ring carbon atom to which they are bound, form a cycloalkyl group having from 5 to 12 carbon atoms; $R_3$ is hydrogen, a straight- or branched chain alkyl residue having from 1 to 12 carbon atoms, an aralkyl residue having from 7 to 12 carbon atoms or a cycloalkyl residue having 5 or 6 carbon atoms; A is -O- or

wherein $R_4$ is hydrogen, a straight- or branched chain alkyl residue having from 1 to 12 carbon atoms and is either unsubstituted or substituted by halogen, cyano or hydroxyl groups or interrupted by one or more oxygen or sulphur atoms, an aralkyl residue having from 7 to 12 carbon atoms, an alkenyl residue having from 3 to 12 carbon atoms or a cycloalkyl residue having from 5 to 12 carbon atoms; $R_5$ is hydrogen, a mono or divalent hydrocarbyl residue having from 1 to 20 carbon atoms and is either unsubstituted or substituted by halogen, cyano or hydroxyl groups or interrupted by one or more oxygen or sulphur atoms, or $R_5$ is a group having the formula II

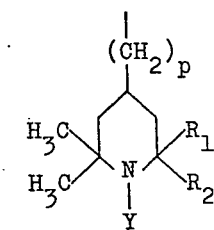

wherein $p$ is 0, 1 or 2, $R_1$ and $R_2$ have their previous significance and Y is hydrogen, a straight- or branched chain alkyl residue having from 1 to 20 carbon atoms, an alkenyl or alkynyl residue having from 3 to 12 carbon atoms, an aralkyl residue having from 7 to 12 carbon atoms or the group $CH_2CH(OH)R_8$ wherein $R_8$ is hydrogen or an alkyl residue having from 1 to 4 carbon atoms or a phenyl residue; and when A is —O—, X is

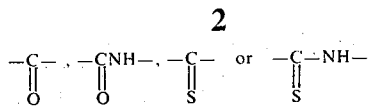

and when A is $>$N—$R_4$, X is

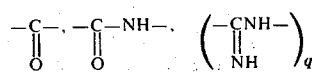

wherein $q$ is 1 or 2

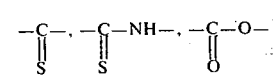

or —SO$_2$—
or when $n$ is 1 and $R_5$ has the foregoing formula II wherein $p$ is 2, X can also be an —SO$_2$NH—,

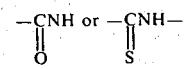

residue; with the provisos that when A is —O—, $R_5$ is not hydrogen and when A is $>$NR$_4$, $m$ is 1, $n$ is 2 and X is

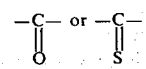

then $R_5$ can be absent.

When $n$ is 1, the substituent $R_5$ may be hydrogen (except when A is —O—), a monovalent straight- or branched aliphatic residue having from 1 to 20 carbon atoms, being saturated or unsaturated and either unsubstituted or substituted by halogen, cyano or hydroxyl groups, or interrupted by one or more oxygen or sulphur atoms, an alicyclic residue having from 5 to 20 carbon atoms an optionally substituted aralkyl residue having from 7 to 12 carbon atoms or an optionally substituted aryl residue having from 6 to 15 carbon atoms, or the group:

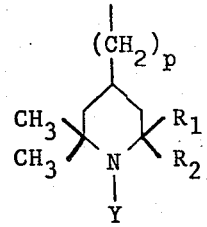

wherein $R_1$, $R_2$, Y and $p$ have their previous significance.

Specific examples of substituent groups $R_5$ include hydrogen (except when A= —O—) methyl, methylthiomethyl, ethyl, 2-hydroxy ethyl, 2-cyanoethyl, n-propyl, isopropyl, n-butyl, 4-chloro-n-butyl, sec-butyl, t-butyl, n-pentyl, neopentyl, 2-ethylpropyl, 2-methylbutyl, n-hexyl, n-octyl, t-octyl, n-dodecanyl, n-octadecanyl, 2-methoxyethyl, 2-n-dodecylthioethyl, allyl, α-methallyl, dec-9-enyl, heptadec-8-enyl, crotyl, cinnamyl, propargyl, 2,4-hexadienyl, benzyl, 2-chloro benzyl, α-methylbenzyl, 4-methoxybenzyl, α,p-dimethylbenzyl, diphenylmethyl, cyclopentyl, cyclohexyl, cyclooctyl, 4-methylcyclohexyl, cyclododecenyl, 9-fluorenyl, adamantyl, phenyl, 4-methylphenyl, 4-t-octylphenyl, α-naphthyl, 4-biphenyl, 2-fluorenyl, 2-chlorophenyl and 4-methoxyphenyl groups.

When $n$ is 2, the substituent $R_5$ may be a divalent straight or branched aliphatic (saturated or unsaturated) residue having 2 to 20 carbon atoms, a divalent alicyclic residue having 5 to 12 carbon atoms, a divalent aralkyl residue having 8 to 12 carbon atoms or a divalent aryl residue having 6 to 15 carbon atoms or, when $m$ is 1 and X is

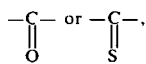

then the substituent $R_5$ may be absent.

Specific examples of substituent groups $R_5$ include 1,2-ethylene, 1,4-n-butylene, 1,3-n-butylene, 1,6-n-hexylene, 1,7-n-heptylene, 1,10-N-decylene, 2,2-dimethyl-1,3-propylene, trimethyl-1,4-butylene, 1,2-vinylene, 3-thia-n-pentane, 3-oxa-n-pentane, 1,4-but-2-enylene, 1,4-but-2-ynylene, 2,5-hex-3-enylene, 1,2-cyclohexylene, 1,4-cyclohexylene, hexahydro-p-xylylene, p-xylylene, m-xylylene, 1,2-phenylene, 1,4-phenylene, 2,2'-biphenylene, 4,4'-biphenylene and 4,4'-biphenylenemethane groups.

Examples of substituents Y in the compounds of formula I include hydrogen, methyl, ethyl, n-propyl, isopropyl, n-butyl, sec-butyl, n-hexyl, n-octyl, n-dodecyl, 2-hydroxyethyl, 2-hydroxypropyl, 2-hydroxy-2-phenylethyl, allyl, α-methallyl, 10-undecenyl, oleyl, benzyl, α-methylbenzyl, p-methylbenzyl, α,p-dimethylbenzyl and α-naphthylmethyl groups.

Particularly preferred substituents Y are hydrogen, straight or branched alkyl residues having from 1 to 4 carbon atoms and the most preferred substituent Y is hydrogen or a methyl group.

Examples of substituents $R_1$ and $R_2$ are methyl, ethyl, n-propyl, isopropyl, n-butyl, sec-butyl, n-hexyl, n-dodecyl, or together with the carbon to which they are bound $R_1$ and $R_2$ can form a group such as:

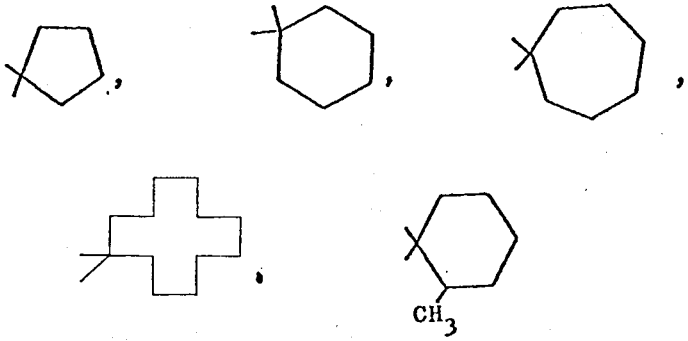

Particularly preferred substituents $R_1$ and $R_2$ are straight or branched alkyl residues having 1 to 4 carbon atoms, and the most preferred substituents $R_1$ and $R_2$ are methyl groups.

Examples of the group $R_3$ include hydrogen, methyl, ethyl, n-propyl, isopropyl, n-butyl, sec-butyl, n-hexyl, n-octyl, n-dodecyl, benzyl, α-methylbenzyl, α,p-dimethylbenzyl, cyclohexyl and cyclopentyl groups.

Particularly preferred alkyl residues are those having from 1 to 8 carbon atoms and the most preferred substituent $R_3$ is hydrogen.

The substituent $R_4$ may be hydrogen, methyl, ethyl, 2-hydroxy ethyl, 2-cyanoethyl, n-propyl, isopropyl, n-butyl, sec-butyl, n-hexyl, n-octyl, n-dodecyl, benzyl, α-methylbenzyl, α,p-dimethylbenzyl, cyclohexyl, cyclopentyl, allyl or α-methallyl, but-3-enyl, 10-undecenyl or propargyl. Particularly preferred substituents $R_4$ are hydrogen and alkyl residues having 1 to 8 carbon atoms and the most preferred is hydrogen.

Preferred groupings X are

and when $n$ is 1, A is — $NR_4$ — and $R_5$ is a residue of formula II as hereinbefore defined wherein $p$ is 2, the preferred group

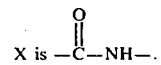

Examples of salts of the compounds of formula I include salts of an inorganic acid, such as phosphates, carbonates, sulphates, chlorides, and the like, as well as organic acid salts, such as acetates, stearates, maleates, citrates, tartrates, oxalates, benzoates and substituted carbamic acids.

Specific examples of compounds of formula I are given in the following list:

a. Where A=>N—$R_4$ 2-(2',2',6',6'-Tetramethylpiperidinyl-4')ethylamine

N-Methyl-2(2',2',6',6'-tetramethylpiperidinyl-4')ethylamine

N-Isopropyl-2(2',2',6',6'tetramethylpiperidinyl-4')ethylamine

N-Benzyl-2(2',2',6',6'-tetramethylpiperidinyl-4')ethylamine

N-n-Octyl-2-(2',2',6',6'-tetramethylpiperidinyl-4')ethylamine

N-Cyclohexyl-2-(2',2',6',6'-tetramethylpiperidinyl-4')ethylamine

N-Acetyl-2-(2',2',6',6'-tetramethylpiperidinyl-4')ethylamine

N-n-Butyryl-2-(2',2',6',6'-tetramethylpiperidinyl-4')ethylamine

N-n-Octanoyl-2-(2',2',6',6'-tetramethylpiperidinyl-4')ethylamine
N-n-Dodecanoyl-2-(2',2',6',6'-tetramethylpiperidinyl-4')ethylamine
N-n-Octadecanoyl-2-(2',2',6',6'-tetramethylpiperidinyl-4')ethylamine
N-Cycloexanoyl-2-(2',2',6',6'-tetramethylpiperidinyl-4')ethylamine
N-Phenylacetyl-2-(2',2',6',6'-tetramethylpiperidinyl-4')ethylamine
N-Benzoyl-2-(2',2',6',6'-tetramethylpiperidinyl-4')ethylamine
N-[(2'',2'',6'',6''-Tetramethylpiperidinyl-4'')acetyl]-2-(2',2',6',6'-tetramethylpiperidinyl-4')ethylamine
N,N'-Di-[2(2',2',6',6'-tetramethylpiperidinyl-4')ethyl]sebacamide
N,N'-Di-[2(2',2',6',6'-tetramethylpiperidinyl-4')ethyl]malonamide
N,N'-Di-[2(2',2',6',6'-tetramethylpiperidinyl-4')ethyl]maleoylamide
N,N'-Di-[2(2',2',6',6'-tetramethylpiperidinyl-4')ethyl]oxalylamide
N,N'-Di-[2(2',2',6',6'-tetramethylpiperidinyl-4')ethyl]thioxalylamide
N,N'-Di-[2'(2'',2'',6'',6''-tetramethylpiperidinyl-4'')ethyl]cyclohexyl-1,4-dicarboxoylamide
N,N'-Di-[2'(2'',2'',6'',6''-tetramethylpiperidinyl-4'')ethyl]phenyl-1,4-dicarboxoylamide
N-Allyl-N'-[2(2',2',6',6'-tetramethylpiperidinyl-4')ethyl]urea
N-Methyl-N'-[2-(2',2',6',6'-tetramethylpiperidinyl-4')ethyl]urea
N-(n-Hexyl)-N'-[2-(2',2',6',6'-tetramethylpiperidinyl-4')ethyl]urea
N-Cyclohexyl-N'-[2-(2',2',6',6'-tetramethylpiperidinyl-4')ethyl]urea
N-Benzyl-N'-[2-(2',2',6',6'-tetramethylpiperidinyl-4')ethyl]urea
N-phenyl-N'-[2(2',2',6',6'-tetramethylpiperidinyl-4')ethyl]urea
N(α-Napthyl)-N'-[2-(2',2',6',6'-tetramethylpiperidinyl-4')ethyl]urea
N,N'-Di[2-(2',2',6',6'-tetramethylpiperidinyl-4')ethyl]urea
1,6-Di[2'(2'',2'',6'',6''-tetramethylpiperidinyl-4')ethylureido]hexane
N,N-Di-cyanoethyl-[2(2',2',6',6'-tetramethylpiperidinyl-4')ethyl-amine]
N-isobutyryl-2(2',2',6',6'-tetramethylpiperidinyl-4')ethylamine.
p,p'-Di[2(2',2',6',6'-tetramethylpiperidinyl-4')ethylureido]-diphenylmethane
[2-(2',2',6',6'-Tetramethylpiperidinyl-4')ethyl]-guanidine
[2-(2',2',6',6'-Tetramethylpiperidinyl-4')ethyl]-biguanidine
N-Thioacetyl-2(2',2',6',6'-tetramethylpiperidinyl-4')ethylamine
N-n-Thiohexanoyl-2-(2',2',6',6'-tetramethylpiperidinyl-4')ethylamine
N-n-Thiododecanoyl-2(2',2',6',6'-tetramethylpiperidinyl-4')ethylamine
N-Phenylthioacetyl-2(2',2',6',6'-tetramethylpiperidinyl-4')ethylamine
N-Thiobenzoyl-2(2',2',6',6'-tetramethylpiperidinyl-4')ethylamine
N-Ethyl-N'[2(2',2',6',6'-tetramethylpiperidinyl-4')ethyl]thiourea
N-Allyl-N'[2-(2',2',6',6'-tetramethylpiperidinyl-4')ethyl]thiourea
N-Cyclohexyl-N'-[2(2',2',6',6'-tetramethylpiperidinyl-4')ethyl]thiourea
N-t-Octyl-N'-[2(2',2',6',6'-tetramethylpiperidinyl-4')ethyl]thiourea
N-(β-Napthyl)-N'-[2(2',2',6',6'-tetramethylpiperidinyl-4')ethyl]thiourea
Ethyl {N-[2(2',2',6',6'-tetramethylpiperidinyl-4')ethyl]} carbamoate
n-n-Butyl {N-[2(2',2',6',6'-tetramethylpiperidinyl-4']} carbamoate
N-[2(2',2',6',6'-tetramethylpiperidinyl-4')ethyl]-p-toluene sulphonamide
Sulphonylaminobis[2(2',2',6',6'-tetramethylpiperidinyl-4')ethane]
2-(1',2',2',6',6'-Pentamethylpiperidinyl-4')ethylamine
2-(1'-n-Propyl-2',2',6',6'-tetramethylpiperidinyl-4')ethylamine
2-(1'-Benzyl-2',2',6',6'-tetramethylpiperidinyl-4')ethylamine
N-Acetyl-2(1',2',2',6',6'-pentamethylpiperidinyl-4')ethylamine
N-n-Butyryl-2(1',2',2',6',6'-pentamethylpiperidinyl-4')ethylamine
N-n-Octanoyl-2(1',2',2',6',6'-pentamethylpiperidinyl-4')ethylamine
2[1'(2''-hydroxyethyl)-2',2',6',6'-tetramethylpiperidinyl-4']ethylamine
2 [1'(2''-phenyl-2''-hydroxyethyl)-2',2',6',6'-tetramethylpiperidinyl-4']ethylamine
N-n-Dodecanoyl-2(1',2',2',6',6'-pentamethylpiperidinyl-4')ethylamine
N-Cyclohexoyl-2(1',2',2',6',6'-pentamethylpiperidinyl-4')ethylamine
N-Phenylacetyl-2(1',2',2',6',6'-pentamethylpiperidinyl-4')ethylamine
N-Benzyl-2(1',2',2',6',6'-pentamethylpiperidinyl-4')ethylamine
N,N'-Di-[2(1',2',2',6',6'-pentamethylpiperidinyl-4')]sebacamide
N-Allyl-N'-[2(1',2',2',6',6'-pentamethylpiperidinyl-4')ethyl]urea
N-Methyl-N'[2(1',2',2',6',6'-pentamethylpiperidinyl-4')ethyl]urea
N-Cyclohexyl-N'[2(1',2',2',6',6'-pentamethylpiperidinyl-4')ethyl]urea
N-Phenyl-N'[2(1',2',2',6',6'-pentamethylpiperidinyl-4')ethyl]urea
N,N'-Di[2(1',2',2',6',6'-pentamethylpiperidinyl-4')ethyl]urea
1,6-Di[2(1',2',2',6',6'-pentamethylpiperidinyl-4')ethylureido]hexane
N-Thioacetyl-2(1',2',2',6',6'-pentamethylpiperidinyl-4')ethylamine
N-Phenylthioacetyl-2(1',2',2',6',6'-pentamethylpiperidinyl-4')ethylamine
N-Methyl-N'[2(1',2',2',6',6'-pentamethylpiperidinyl-4')ethyl]thiourea
N-Cyclohexyl-N'[2(1',2',2',6',6'-pentamethylpiperidinyl-4')ethyl]thiourea N-(β-Naphthyl)-N'[2(1',2',2',6',6'-pentamethyl-piperidinyl-4')ethyl]thiourea
Ethyl N[2(1',2',2',6',6'-pentamethylpiperidinyl-4')ethyl] carbamoate
N-[2(1',2',2',6',6'-Pentamethylpiperidinyl-4)ethyl]p-toulenesulphonamide
N-Acetyl-2(1'-allyl-2',2',6',6'-tetramethylpiperidinyl-4')ethylamine
N-Benzoyl-2(1'-n-propyl-2,2,6,6-tetramethyl-piperidinyl-4')ethylamine
N-Methyl-N-[2(1'-dodecyl-2',2',6',6'-tetramethyl-piperidinyl-4')ethyl]urea
N-n-Octanoyl-2(2',2'-di-isopropyl-6',6'-dimethyl-piperidinyl-4')ethylamine
N-Phenyl-N'[2(2,2-diethyl-6',6'-dimethylpiperidinyl-4')ethyl]urea
N-(2''-hydroxyethyl)[2-(1',2',2',6',6'-pentamethyl-piperidinyl-4')]ethylamine
N,N-Di(2''-hydroxyethyl)[2-(2',2',6',6'-tetramethylpiperidinyl-4')]ethylamine
N,N-Di(2''-hydroxyethyl)[2-(1',2',2',6',6'-pentamethylpiperidinyl-4')]ethylamine
N,N'-Di[2(2',2',6',6'-tetramethylpiperidinyl-4')ethyl]thiodipropionamide b. Where A is —O—
[2(2',2',6',6'-Tetramethylpiperidinyl-4')ethyl]-n-dodecanoate
n-Octyl-[2(2',2',6',6'-tetramethylpiperidinyl-4')ethyl]ether
N-Phenyl[2(2',2',6',6'-tetramethylpiperidinyl-4')ethyl]urethane
N-Methyl[2(2',2',6',6'-tetramethy piperidinyl-4')ethyl]urethane
N-Cyclohexyl[2(2',2',6',6'-tetramethylpiperidinyl-4')ethyl]urethane
[2(2',2',6',6'-Tetramethylpiperidinyl-4')ethyl](2'',2'',6'',6''-tetramethylpiperidinyl-4'')acetate The present invention also provides a first process in which a compound of formula I wherein m is 0, A is >N—R$_4$ and R$_5$ is hydrogen is produced, comprising hydrogenating a compound having the formula:

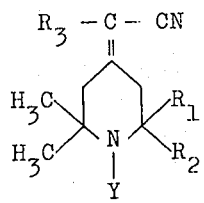

III wherein R$_1$,R$_2$,R$_3$ and Y have their previous significance with the proviso that Y is a saturated residue, in the presence of an amine R$_4$NH$_2$ wherein R$_4$ has its previous significance provided that R$_4$ is a saturated residue.

The hydrogenation of the compound of formula III may be conveniently effected using molecular hydrogen or using chemical means such as lithium aluminium hydride. If molecular hydrogen is used, the hydrogenation may be conducted in known manner using a hydrogenation catalyst such as palladium, platinum, rhodium or nickel, preferably supported on a carrier such as silica, calcium carbonate or carbon. Advantageously, the reaction is conducted at an elevated temperature and pressure and in a suitable solvent such as ethanol or cyclohexane.

The compounds of formula I (wherein A =>NR$_4$) may also be prepared by reacting a compound having the formula:-

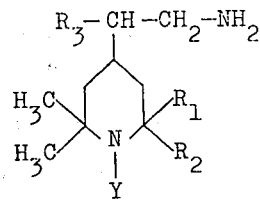

IV wherein R$_1$, R$_2$, R$_3$ and Y have their previous significance, with the corresponding aldehyde and formic acid, viz using a Leuckart reaction.

In a further modification, the compound of formula IV may be reacted with the corresponding aldehyde and the Schiff base so obtained may then be hydrogenated over a catalyst such as nickel or palladium. This reaction cannot be used to prepare compounds of formula I in which the substituents R$_4$ and Y are unsaturated, since such substituents would be hydrogenated during the process.

In a still further modification, the compound of formula IV may be reacted with an alkyl, alkenyl, cycloalkyl or aralkyl halide.

Starting-materials of formula III may be prepared by the reaction, in an inert solvent, of a phosphonate having the formula:

[(R$_6$O)$_2$P(O)CH(R$_3$)CN ]$^-$B$^+$     V wherein R$_3$ has its previous significance, R$_6$ is an alkyl residue having from 1 to 4 carbon atoms and B$^+$ is an organic or inorganic base cation, with a piperidine derivative having the formula:

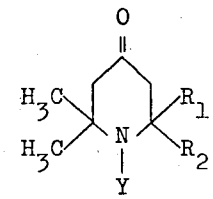

VI wherein R$_1$,R$_2$ and Y have their previous significance with the proviso that Y is not an unsaturated residue.

Suitable examples of inert solvents are benzene, dioxan and cyclohexane, and base cations B+ which may be used are alkali metal cations.

The compounds of formula V are well-known.

The substituent Y when it is other than hydrogen can be introduced into the corresponding compounds of formula I, III, or VI where Y is H by conventional methods such as by reaction with an alkyl, aralkyl, alkenyl or alkynyl halide or by a Leuckart or Wallach reaction, or by the reaction with

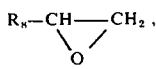

wherein $R_8$ has its previous significance.

The present invention also provides a process of producing a compound of formula I wherein m is 0, A is >N—$R_4$ and one or both of $R_4$ and $R_5$ is a —$CH_2$CH(OH)$R_8$ residue comprising reacting a compound of formula IV as hereinbefore defined with a compound of formula:

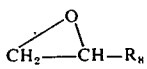

wherein $R_8$ has its previous significance.

The present invention further provides a process of producing a compound of formula I wherein m is 1 comprising reacting a compound having the formula:

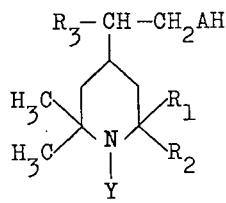
VII wherein $R_1$, $R_2$, $R_3$, A and Y have their previous significance, with a compound VIII capable of introducing a group —$XR_5$ on to the nitrogen or oxygen atom of the side-chain.

The compounds of formula VII where A = —O— are described in our co-pending British Pat. application No. 5470/73.

In a further process, a compound of formula I wherein A is >N—$R_4$ and one or both of $R_4$ and $R_5$ is a cyanoethyl group is produced by reacting a compound of formula VII with acrylonitrile.

The reactants VIII capable of introducing the group —$XR_5$ will of course vary according to the nature of the group X. Suitable reactants may, however, be summarised under the following headings:

I. A is >N—$R_4$ or —O—
  i. X is —CO or —CS
    a. Suitable reactants are those having the formula:
      $R_5(COZ)_n$ or $R_5(CSZ)_n$
    wherein $R_5$ and $n$ have their previous significance and Z is halogen; for example when $n$ is 1, suitable reactants are butyryl chloride, acetyl chloride, benzoyl chloride, crotonyl chloride; when $n$ = 2 suitable reagents are sebacoyl chloride, fumarylchloride, succinyl chloride, adipyl, chloride, alternatively when $R_5$ is absent a suitable reactant is, for example, oxalyl chloride.

This reaction is preferably effected in an inert solvent such as benzene or cyclohexane.
    b. Other suitable reactants are those having the formula:
      $R_5(CO_2R_7)_n$ or $R_5(CSOR_7)_n$
    wherein $R_5$ and n have their previous significance and $R_7$ is an alkyl residue having 1 to 4 carbon atoms. Suitable reactant in this group is, for example, ethylbenzoate, ethyl(2,2,6,6-tetra-methylpiperidinyl-4)acetate and methyloctanoate.

This reaction may be effected at a temperature within the range of from 0° to 200°C but is preferably conducted at a temperature within the range of from 140° to 180°C. The reaction may be carried out in the presence or absence of catalyst and inert solvent such as xylene. However, if a catalyst is used it may be, for example an alkali metal amide, p-toluene sulphonic acid, tetra-butyl titanate or an alkali metal alkoxide.
  ii.
    (a) X is —CONH— or —CSNH—
      Examples of reactants are those having the formula:
        $R_5(NCO)_n$ or $R_5(NCS)_n$
      wherein $R_5$ and $n$ have their previous significance, for example when n=1 methyl isocyanate, cyclohexyl isocyanate, phenyl isocyanate, 1-naphthyl isothiocyanate and when n=2, Hexane-1,6-diisocyanate, 4,4'-diisocyanatediphenyl methane.

The reaction may be conveniently effected in a suitable solvent such as petroleum ether, cyclohexane or benzene and with, or without a catalyst such as diazobiscyclooctane or piperidine.

II. X is >N—$R_4$ only
  i.
    a. X is

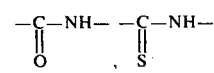

or $SO_2NH$—, when $R_5$ has the formula II wherein $p$ is 2.
Those compounds of formula I in which $R_5$ has the formula:

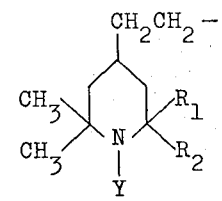

wherein $R_1$, $R_2$ and Y have their previous significance and
  b.

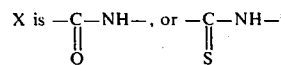

may be produced by reacting the compound of formula VII with phosgene (or urea) or thiophosgene (or thiourea or carbon disulphide together with an alkali metal hydroxide) respectively.
    c. When X is —$SO_2$—NH—, compounds of formula I are produced by the reaction of compounds of formula IV with sulphuryl chloride.
  ii.

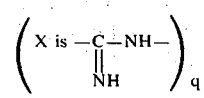

wherein q has its previous significance.

a. Those compounds in which $q$ is 1 may be produced for instance by reaction of the compound of formula IV with a cyanamide or substituted cyanamide having the formula $R_5NHCN$, wherein $R_5$ has its previous significance.

b. The compounds in which $q$ is 2 may be prepared for instance by reaction of the compound of formula IV with a dicyandiamide or substituted dicyandiamide having the formula

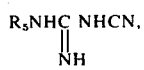

wherein $R_5$ has its previous significance.

iii. X is $-SO_2-$

These compounds may be prepared by reaction of a compound of formula IV with a compound having the formula $R_5(SO_2Z)_n$ wherein $R_5$ and n have their previous significance and Z is halogen, for example p-toluenesulphonyl chloride.

III. A= —O— and m is absent i. A compound of formula VII where A = —O— is reacted with an alkali metal to give the alkali metal salt, and then with a compound of formula $R_5Z$ where Z is an halogen atom.

ii. Alternatively a compound of formula IX

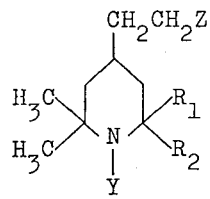

IX where Z is an halogen atom may be reacted with compounds of formula $R_5OM$ where M is an alkali metal.

Compounds of formula IX may be prepared from compounds of formula VII where A is —O— and $R_3$ is H by methods known in the art.

The reactions under heading III may be carried out in a solvent inert to the reactants for instance toluene, cyclohexane, preferably at the reflux temperature of the solvents.

Salts of the compounds of formula I are also new compounds and form part of this invention. The salts may be produced by the reaction of an acid with a compound of formula I in an inert solvent, preferably at ambient temperature although higher reaction temperatures may be employed if desired.

The compounds of formula I, or the salts thereof, may be isolated and purified, after their production as hereinbefore described, by any conventional technique, such as fractional crystallisation from a suitable solvent.

The compounds of formula I and the salts thereof, when incorporated into a polymeric substrate, provide protection to the substrate against deterioration caused by visible and/or ultra-violet light, oxidative degradation or thermal effects.

The present invention still further provides a composition comprising an organic material and a stabilising amount of a compound having the formula I as hereinbefore defined.

Compounds of formula I have been found to impart to polyolefines an exceptionally high degree of stability towards deterioration normally induced by the effects of ultra-violet radiation or exposure to heat. Moreover, this improved stability is achieved without affecting the colour properties of the treated polyolefine. The stabilisers of the invention provide effective light and/or heat stabilisation, especially for low- and high-density polyethylene and polypropylene and polystyrene as well as polymers of butene-1, pentene-1, 3-methylbutene-1, hexene-1, 4-methylpentene-1, 4-methylhexene-1 and 4,4-dimethyl-pentene-1, and also co- and terpolymers of olefines, particularly of ethylene or propylene.

Other organic materials susceptible to degradation by the effects of light and the properties of which are improved by the incorporation therein of a compound of Formula I include natural and synthetic polymeric materials, for instance natural and synthetic rubbers, the latter including, for example, homo-, co- and terpolymers of acrylonitrile, butadiene and styrene.

Specific synthetic polymers include polyvinyl chloride and vinyl chloride co-polymers, polyvinyl acetate as well as condensation polymers derived from ether, ester (derived from carboxylic, sulphonic or carbonic acids) amide or urethane compounds; polyvinyl acetals; polyacrylates such as polymers and copolymers of methyl acrylate, ethyl acrylate, methyl methacrylate and ethyl methacrylate; polyamides; ureaformaldehyde and melamine-formaldehyde resins; cellulose plastics such as cellulose acetate, cellulose butyrate and cellulose nitrate. Certain of these polymers can, for instance, form the basis of surface coating media such as paints and lacquers having an oil or resin base, such as an alkyd or polyamide resin.

The amount of the compound of formula I which is incorporated into the organic material in order to achieve maximal protection against degradation by light varies according to the properties of the organic material treated and according to the severity of the light radiation and to the length of exposure. However, for most purposes it is sufficient to use an amount of the compound of formula I within the range of from 0.01% to 5% by weight, more preferably within the range of from 0.1% to 2% by weight based on the weight of untreated organic material.

The compounds of formula I may be incorporated into the polymeric material by any of the known techniques for compounding additives with a polymer. For example, the compound of formula I and the polymer may be compounded in an internal mixer. Alternatively, the compound of formula I may be added as a solution or slurry in a suitable solvent or dispersant, for instance an inert organic solvent such as methanol, ethanol or acetone to powdered polymer and the whole mixed intimately in a mixer, and the solvent subsequently removed. As a further alternative the compound of formula I may be added to the polymer during the preparation of the latter, for instance at the latex stage of polymer production, to provide pre-stabilised polymer material.

Optionally, the composition of the invention may contain further additives, especially those used in polymer formulations, such as antioxidants of the phenol or amine type, U.V. absorbers and light protectants, phosphite stabilisers, peroxide decomposers, polyamide stabilisers, basic co-stabilisers, polyvinyl chloride stabilisers, nucleation agents, plasticizers, lubricants, emulsifiers, anti-static agents, flame-protectants, pigments, carbon black, asbestos, glass fibres, kaolin and talc.

The present invention therefore includes binary, tertiary and multi-component compositions containing the stabiliser of formula I together with one or more functional additives for polymers.

Examples of suitable antioxidants are those of the hindered phenol type such as those selected from the following groups:

1. Phenolic compounds having the general formula
   Q—(CH$_2$)$_w$—A
   wherein
   Q is

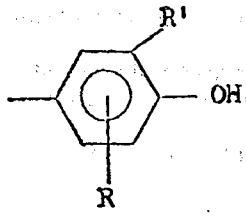

A is —
   CR(COOR'')$_2$

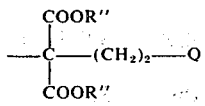

R is hydrogen or lower alkyl
R' is lower alkyl
R'' is alkyl group having from 6–24 carbon atoms
w is an integer from 0 to 4.

Illustrative examples of the compounds shown above are
   di-n-octadecyl α-(3,5-di-t-butyl-4-hydroxybenzyl)-malonate
   di-n-octadecyl α-(3-t-butyl-4-hydroxy-5-methyl-benzyl) malonate
   di-n-octadecyl-α,α'bis-(3-t-butyl-4-hydroxy-5-methylbenzyl) malonate 2. Phenolic compounds having the general formula
   Q—R Illustrative examples of the compounds shown above are
   2,6-di-t-butyl-p-cresol
   2-methyl-4,6-di-t-butylphenol and the like.
   2,6-di-Octadecyl-p-cresol 3. Phenolic compounds having the formula
   Q—C$_w$H$_{2w}$—Q Illustrative examples of the compounds shown are:
   2,2'-methylene-bis(6-t-butyl-4-methylphenol)
   2,2'-methylene-bis(6-t-butyl-4-ethylphenol)
   4,4'-butylidene-bis(2,6-di-t-butylphenol)
   4,4'-(2-butylidene)-bis(2-t-butyl-5-methylphenol)
   2,2'-methylene-bis[6-(2-t-methylcyclohexyl)-4-methylphenol]
   2,2'-methylene-bis(3-t-butyl-5-ethylphenol)
   4,4'-methylene-bis(3,5-di-t-butylphenol)
   4,4'-methylene-bis(3-t-butyl-5-methylphenol)
   2,2'-methylene-bis(3-t-butyl-5-methylphenol) and the like.

4. Phenolic compounds having the formula
   R—O—Q

Illustrative examples of such compounds are
   2,5-di-t-butylhydroquinone
   2,6-di-t-butylhydroquinone
   2,5-di-t-butyl-4-hydroxyanisole 5. Phenolic compounds having the formula
   Q—S—Q Illustrative examples of such compounds are
   4,4'-thiobis-(2-t-butyl-5-methylphenol)
   4,4'-thiobis-(2-t-butyl-6-methylphenol)
   2,2'-thiobis-(6-t-butyl-4-methylphenol)
   4,4'-thiobis-(2-methyl-5-t-butylphenol)

6. Phenolic compounds having the formula

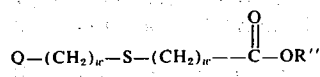

Illustrative examples of such compounds are octadecyl-(3,5-dimethyl-4-hydroxybenzylthio)-acetate dodecyl-(3,5-di-t-butyl-4-hydroxybenzylthio)-propionate 7. Phenolic compounds having the formula

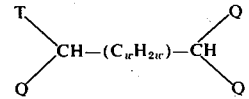

wherein
   T is hydrogen
   R or Q as defined above.

Illustrative examples of such compounds are
   1,1,3-tris(3,5-dimethyl-4-hydroxyphenyl)-propane
   1,1,3-tris(5-t-butyl-4-hydroxy-2-methylphenyl)-butane
   1,1,5,5-tetrakis-(3'-t-butyl-4'-hydroxy-6'-methylphenyl)-n-pentane 8. Phenolic compounds having the formula

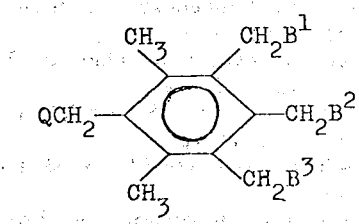

wherein B$^1$, B$^2$ and B$^3$ are hydrogen, methyl or provided that when B$^1$ and B$^3$ are Q then B$^2$ is hydrogen or methyl and when B$^2$ is Q then B$^1$ and B$^3$ are hydrogen or methyl.

Illustrative examples of such compounds are
   1,4-di(3,5-di-t-butyl-4-hydroxybenzyl)-2,3,5,6-tetramethylbenzene
   1,3,5-tri(3,5-di-t-butyl-4-hydroxybenzyl)-2,4,6-trimethylbenzene 9. Phenolic compounds having the formula

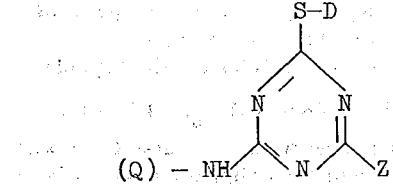

wherein Z is NHQ, —S—D or —O—Q D is alkyl group having from 6–12 carbon atoms or —(C$_w$H$_{2w}$)—S—R''
Illustrative examples of such compounds are 2,4-bis-(n-octylthio)-6-(3,5-di-t-butyl-4-hydroxyaniline)-1,3,5-triazine
6-(4-hydroxy-3-methyl-5-t-butylanilino)-2,4-bis-(n-octyl-thio-1,3,5-triazine
6-(4-hydroxy-3,5-dimethylanilino)-2,4-bis-(n-octylthio)-1,3,5-triazine
6-(4-hydroxy-3,5-di-t-butylanilino)-2,4-bis-(n-octylthio)-1,3,5-triazine.
6-(4-hydroxy-3,5-di-t-butylanilino)-4-(4-hydroxy-3,5-di-t-butylphenoxy)-2-(n-octylthio-1,3,5-triazine
2,4-bis(4-hydroxy-3,5-di-t-butylanilino)-6-(n-octylthio)-1,3,5-triazine.

10. Phenolic compounds having the formula

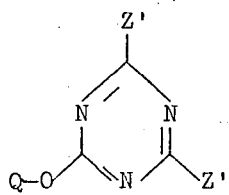

wherein Z' is —O—Q, —S—D or —S—($C_uH_{2u}$)—SD
Illustrative examples of such compounds are
2,3-bis-(3,5-di-t-butyl-4-hydroxyphenoxy)-6-(n-octylthio)-1,3,5-triazine
2,4,6-tris-(4-hydroxy-3,5-di-t-butylphenoxy)-1,3,5-triazine.
6-(4-hydroxy-3,5-di-t-butylphenoxy)-2,4-bis-(n-octylthio-ethylthio)-1,3,5-triazine
6-(4-hydroxy-3-methylphenoxy)-2,4-bis-(n-octylthio)-1,3,5-triazine
6-(4-hydroxy-3-t-butylphenoxy)-2,4-bis-(n-octylthioethylthio)-1,3,5-triazine
6-(4-hydroxy-3-methyl-5-t-butylphenoxy)-2,4-bis-(n-octylthio)-1,3,5-triazine
2,4-bis-(4-hydroxy-3-methyl-5-t-butylphenoxy)-6-(n-octylthio)-1,3,5-triazine
2,4,6-tris-(4-hydroxy-3-methyl-5-t-butylphenoxy)-1,3,5-triazine
6-(4-hydroxy-3,5-di-t-butylphenoxy)-2,4-bis-(n-octylthio-propylthio)-1,3,5-triazine
6-(4-hydroxy-3,5-di-t-butylphenoxy)-2,4-bis-(n-dodecylthioethylthio)-1,3,5-triazine
2,4-bis-(4-hydroxy-3,5-di-t-butylphenoxy)-6-butylthio-1,3,5-triazine
2,4-bis-(4-hydroxy-3,5-di-t-butylphenoxy)-6-(n-octadecylthio)-1,3,5-triazine
2,4-bis-(4-hydroxy-3,5-di-t-butylphenoxy)-6-(n-dodecylthio)-1,3,5-triazine
2,4-bis-(4-hydroxy-3,5-di-t-butylphenoxy)-6-(n-octylthio-propylthio)-1,3,5-triazine
2,4-bis-(4-hydroxy-3,5-di-t-butylphenoxy)-6-(n-octylthioethylthio)-1,3,5-triazine
2,4-bis-(4-hydroxy-3,5-di-t-butylphenoxy)-6-(n-dodecylthioethylthio)-1,3,5-triazine.

11. Phenolic compounds having the formula

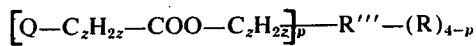

wherein p is an integer from 2 to 4 and R''' is a tetravalent radical selected from aliphatic hydrocarbons having from 1 to 30 carbon atoms
aliphatic mono and dithioethers having from 1 to 30 carbon atoms
aliphatic mono and diethers having from 1 to 30 carbon atoms and z is an integer from 0 to 6.

Illustrative examples of such compounds are

Sub-class I n-Octadecyl 3-(3,5-di-t-butyl-4-hydroxyphenyl)-propionate
n-Octadecyl 2-(3,5-di-t-butyl-4-hydroxyphenyl)-acetate
n-Octadecyl 3,5-di-t-butyl-4-hydroxybenzoate
n-Hexyl 3,5-di-t-butyl-4-hydroxyphenylbenzoate
n-Dodecyl 3,5-di-t-butyl-4-hydroxyphenylbenzoate
Neo-dodecyl 3-(3,5-di-t-butyl-4-hydroxyphenyl)-propionate
Dodecyl β-(3,5-di-t-butyl-4-hydroxyphenyl)-propionate
Ethyl α-(4-hydroxy-3,5-di-t-butylphenyl)-isobutyrate
Octadecyl α-(4-hydroxy-3,5-di-t-butylphenyl)-isobutyrate
Octadecyl α-(4-hydroxy-3,5-di-t-butylphenyl)-propionate Sub-class II 2-(n-octylthio)ethyl 3,5-di-t-butyl-4-hydroxybenzoate
2-(n-octylthio)ethyl 3,5-di-t-butyl-4-hydroxyphenylacetate
2-(n-octadecylthio)ethyl 3,5-di-t-butyl-4-hydroxyphenylacetate
2-(n-octadecylthio)ethyl 3,5-di-t-butyl-4-hydroxybenzoate
2-(2-hydroxyethylthio)ethyl 3,5-di-t-butyl-4-hydroxybenzoate
2,2'-thiodiethanol bis(3,5-di-t-butyl-4-hydroxyphenyl)acetate
Diethyl glycol bis-[3,5-di-t-butyl-4-hydroxyphenyl)propionate]
2-(n-octadecylthio)ethyl 3-(3,5-di-t-butyl-4-hydroxyphenyl)propionate
2,2'-Thiodiethanol-bis-3-(3,5-di-t-butyl-4-hydroxyphenyl)propionate
Stearamido N,N-bis-[ethylene 3-(3,5-di-t-butyl-4-hydroxyphenyl)propionate]
n-Butylimino N,N-bis-[ethylene 3-(3,5-di-t-butyl-4-hydroxyphenyl)propionate]
2-(2-stearoyloxyethylthio)ethyl 3,5-di-t-butyl-4-hydroxybenzoate
2-(2-hydroxyethylthio)ethyl 7-(3-methyl-5-t-butyl-4-hydroxyphenyl)heptanoate
2-(2-stearoyloxyethylthio)ethyl 7-(3-methyl-5-t-butyl-4-hydroxyphenyl)heptanoate Sub-class III 1,2-propylene glycol bis-[3-(3,5-di-t-butyl-4-hydroxyphenyl)propionate]
Ethylene glycol bis-[3-(3,5-di-t-butyl-4-hydroxyphenyl)propionate]
Neopentylglycol bis-[3-(3,5-di-t-butyl-4-hydroxyphenyl)propionate]
Ethylene glycol bis-(3,5-di-t-butyl-4-hydroxyphenylacetate)
Glycerine-1-n-octadecanoate-2,3-bis-(3,5-di-t-butyl-4-hydroxyphenylacetate
Pentaethylthritol-tetrakis-[3-(3,5-di-t-butyl-4-hydroxyphenyl)propionate]
1,1,1-trimethylol ethane-tris-3-(3,5-di-t-butyl-4-hydroxyphenyl)propionate
Sorbitol hexa-[3-(3,5-di-t-butyl-4-hydroxyphenyl)propionate]

1,2,3-butanetriol tris[3-(3,5-di-t-butyl-4-hydroxyphenyl)propionate]
2-hydroxyethyl 7-(3-methyl-5-t-butyl-4-hydroxyphenyl)heptanoate
2-stearoyloxyethyl 7-(3-methyl-5-t-butyl-4-hydroxyphenyl)heptanoate heptanoate
1,6-n-hexanediol-bis[(3',5'-di-t-butyl-4-hydroxyphenyl)propionate]

12. Phenolic compounds having the formula

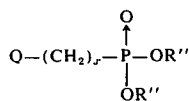

where x is an integer of 1 to 2.

Illustrative examples of such compounds are
Di-n-octadecyl 3,5-di-t-butyl-4-hydroxybenzylphosphonate
Di-n-octadecyl 3-t-butyl-4-hydroxy-5-methylbenzylphosphonate
Di-n-octadecyl 1-(3,5-di-t-butyl-4-hydroxyphenyl)-ethane-phosphonate
Di-n-tetradecyl 3,5-di-t-butyl-4-hydroxybenzylphosphonate
Di-n-hexadecyl 3,5-di-t-butyl-4-hydroxybenzylphosphonate
Di-n-docosyl-3,5-di-t-butyl-4-hydroxybenzylphosphonate
Di-n-octadecyl 3,5-di-t-butyl-4-hydroxybenzylphosphonate 13. Phenolic compounds having the formula

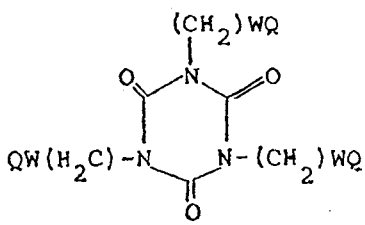

wherein W and Q are defined above.

Illustrative examples of such compounds are:
tris-(3,5-di-t-butyl-4-hydroxybenzyl)isocyanurate
tris-(3-t-butyl-4-hydroxy-5-methylbenzyl)isocyanurate The above phenolic hydrocarbon stabilizers are known and many are commercially available.

While any of the above mentioned antioxidants can be useful in combination with the ultraviolet light stabilizers of this invention, the preferred antioxidants consist of the hindered phenols in groups 1, 8, 9, 10, 11, 12 and 13 as mentioned above. The most preferred hindered phenols are those of groups 1, 9, 11, 12 and 13.

Further examples of antioxidants are those of the aminoaryl series for instance aniline and naphthylamine derivatives as well as their heterocyclic derivatives such as:
phenyl-1-naphthylamine
phenyl-2-napthylamine
N,N'-diphenyl-p-phenyldiamine
N,N'-di-sec.butyl-p-phenylenediamine
6-Ethoxy-2,2,4-trimethyl-1,2-dihydroquinoline
6-Dodecyl-2,2,4-trimethyl-1,2-dihydroquinoline
Mono- and di-octyliminodibenzyl and polymerised 2,2,4-trimethyl-1,2-dihydroquinoline.

Ultraviolet absorbers and light protectants include
a. 2-(2'-hydroxyphenyl)benzotriazoles, for instance 5'-methyl; 3',5'-di-t-butyl; 5'-t-butyl; 5-chloro-3',-5'-di-t-butyl; 5-chloro-3'-t-butyl-5'-methyl; 3'-sec.-butyl-5'-tert.butyl; 3'-[α-methylbenzyl]-5'-methyl-; 3'-[α-methylbenzyl)-5'-methyl-5-chloro-; 4'-octoxy-; 3',5'-di-t-amyl; 3'-methyl-5'-carbomethoxyethyl; 5-chloro-3',5'-di-t-amyl derivatives.
b. 2,4-bis-(2'-hydroxyphenyl)-6-alkyl-S-triazines, for instance the 6-ethyl or 6-undecyl derivatives.
c. 2-hydroxybenzophenones; for instance the 4-hydroxy, 4-methoxy, 4-octoxy-, 4-decyloxy-, 4-dodecyloxy-, 4,2',4'-trihydroxy or 2'-hydroxy-4,4'-dimethoxy derivatives.
d. 1,3-Bis(2'-hydroxybenzoyl)-benzenes for instance,
1,3-bis-(2'-hydroxy-4'-hexyloxybenzoyl)benzene
1,3-bis-(2'-hydroxy-4'-octoxybenzoyl)benzene
1,3-bis-(2'-hydroxy-4'-dodecyloxybenzoyl)benzene
e. Aryl esters from optionally substituted benzoic acids such as phenylsalicylate, octylphenylsalicylate, dibenzoyl resorcinol, bis-(4-tert.butylbenzoyl) resorcinol, benzoylresorcinol and 3,5-di-tert.butyl-4-hydroxy-benzoic acid-2,4-di-tert.butyl phenyl ester and - octadecyl ester and -2-methyl-4,6-di-tert. butyl phenyl ester.
f. Acrylates, for instance α-Cyano-β,β-diphenylacrylic acid ethyl- or iso-octyl ester, α-carbomethoxycinnamic acid methyl- or butyl ester and N-(β-carbomethoxyvinyl)-2-methyl indoline.
g. Nickel compounds such as nickel complexes of 2,2'-thiobis-(4-tert. octylphenol), for instance the 1:1 and 1:2 complexes, optionally having other ligands such as n-butylamine, triethanolamine or N-cyclohexyl-diethanolamine; nickel complexes of bis-(4-tert. octylphenyl) sulphone such as the 2:1 complex, optionally having other ligands such as 2-ethylcapric acid; nickel dibutyl dithiocarbamates; nickel salts of 4-hydroxy-3,5-di-tert.butylbenzyl)-phosphonic acid mono-alkyl esters such as the methyl-, ethyl- or butyl esters; the nickel complex of 2-hydroxy-4-methyl-phenyl-undecylketonoxime; and nickel-3,5-di-tert.butyl-4-hydroxy benzoate, and
h. Oxalic acid diamides, for instance
4,4'-dioctyloxyoxanilide
2,2'-dioctyloxy-5,5'-di-tert.butyl-oxanilide
2,2'-di-dodecyloxy-5,5'-di-tert.butyl oxanilide
2-ethoxy-5-tertiarybutyl-2'-ethyl-oxanilide
2-ethoxy-2'-ethyl-oxanilide mixtures of o- and p-methoxy and ethoxy- disubstituted oxanilides and the compound of formula:

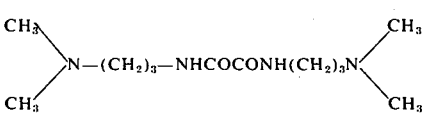

Phosphite stabilisers include triphenyl phosphite, diphenylalkyl phosphites, phenyl dialkyl phosphites, trinonylphenyl phosphite, trilauryl phosphite, trioctadecyl phosphite, 3,9-di-isodecyloxy-2,4,8,10-tetraoxa- 3,9-diphosphaspiro-(5,5)-undecane and tri-(4-hydroxy-3,5-di-tert. butylphenyl)phosphite.

Peroxide-decomposing compounds for polyolefins include esters of β-thiodipropionic acids, for instance the lauryl-, stearyl-, myristyl- or tridecyl esters, salts of mercaptobenzimidazoles such as the zinc salt and diphenylthiourea.

Suitable polyamide stabilisers include copper salts in combination with iodides and/or further phosphorus compounds and salts of bivalent manganese.

Basic co-stabilisers are, for example, polyvinylpyrrolidone, melamine, benzoguanamine, triallyl cyanurate, dicyandiamide, urea derivatives, hydrazine derivatives, amines, polyamides, polyurethanes, alkali and alkaline earth salts of higher saturated or unsaturated fatty acids such as calcium stearate.

Polyvinyl chloride stabilisers include organotin compounds, organo lead compounds and Ba/Cd salts of fatty acids.

Examples of nucleation agents are 4-tert.butyl benzoic acid, adipic acid and diphenylacetic acid.

As with the compound of formula I, any further additive is advantageously employed in a proportion within the range of from 0.01% to 5% by weight, based on the weight of untreated polymeric material.

In binary combinations with one or more antioxidants listed above or in tertiary combinations with such antioxidants and U.V. absorbers listed above, the compounds of formula I provide very effective stabiliser packages in polyolefine formulations.

Some Examples will now be given. Parts and percentages are by weight unless otherwise stated.

EXAMPLE 1 a. A mixture of 450 parts by weight of diethyl phosphonoacetonitrile, 380 parts by weight of 2,2,6,6-tetramethylpiperidin-4-one, and 135 parts by weight of sodium methoxide in 2500 parts by volume of ethyl alcohol was heated together with stirring at reflux for six hours. The solvent was then removed by distillation under reduced pressure, the residue was treated with water (1500 parts by volume) and the resulting oil was extracted with ether (6 × 200 parts by volume). The combined ether extracts were dried over magnesium sulfate and the ether was removed by distillation under reduced pressure. Distillation of the residual oil gave 302 parts by weight of (2,2,6,6-tetramethylpiperidinylidene-4) acetonitrile, boiling point 130°—2°C/12 mm Hg.

b. This material was hydrogenated in 1500 parts by volume of methyl alcohol saturated by ammonia at a pressure of 60 atmospheres hydrogen and 60°C over 12 hours using Raney Nickel catalyst. After removal of the catalyst and solvent, there was obtained by distillation, 250 parts by volume (80% theory yield) of pure 2(2′,2′,6′,6′-tetramethylpiperidinyl-4′) ethylamine, boiling at 110°–2°C/12mm Hg and having the following elemental analysis by weight:

|  | C | H | N |  |
|---|---|---|---|---|
| Found | 71.49 | 12.81 | 15.32 | % |
| Required for $C_{11}H_{24}N_2$ | 71.70 | 13.12 | 15.20 | % |

EXAMPLE 2 a. 60 Parts by weight of (2,2,6,6-tetramethylpiperidinyl-idene-4)acetonitrile (produced as in Example 1), 31.4 parts by volume of formic acid (98%) and 28.2 parts by volume of 36% aqueous formaldehyde were heated with stirring at 100°C for four hours.

The cooled solution was basified with 46% aqueous sodium hydroxide and the resulting oil extracted with 4.50 parts by volume of ether. The combined ether extracts were dried over magnesium sulphate and the ether removed by distillation under reduced pressure. The residual oil was purified by distillation to give 56 parts by weight (86% of theory yield) of (1,2,2,6,6-pentamethylpiperidinylidene-4)acetonitrile boiling at 152°C/ 20 mm Hg.

b. This material was hydrogenated in 250 parts by volume of methyl alcohol saturated with ammonia at a pressure of 100 atmospheres and at 100°C over 24 hours using Raney Nickel catalyst. After removal of the solvent and catalyst the residual oil was purified by distillation to give 45 parts by weight (78% of theory yield) of 2(1′,2′,2′,6′,6′-pentamethylpiperidinyl-4′)ethylamine boiling at 82°–4°C/1.0 mm Hg, and having the following elemental analysis by weight:

|  | C | H | N |  |
|---|---|---|---|---|
| Found | 72.58 | 13.00 | 13.97 | % |
| Required for $C_{12}H_{26}N_2$ | 72.66 | 13.21 | 14.12 | % |

EXAMPLE 3

A mixture of 3.1 parts by weight of methyl isocyanate, 9.2 parts by weight of 2(2′,2′,6′,6′-tetramethylpiperidinyl-4′)ethylamine and 100 parts by volume of petroleum ether (boiling range 60°–80°C.) was heated at reflux for 24 hours with a trace amount of diazobiscyclooctane.

The petroleum ether was removed by distillation under reduced pressure to give an oil which solidified on standing. This was dissolved in 50 parts by volume of carbon tetrachloride and reprecipitated by the addition of 200 parts by volume of petroleum ether (boiling range 60°–80°C.). The white solid was collected by filtration and dried at 50°C. to give 10.3 parts by weight (86% of theory yield) of pure N-methyl-N′-[2(2′,2′,-6′,6′-tetramethylpiperidinyl-4′)ethyl]urea, melting at 73°C, and having the following elemental analysis by weight:

|  | C | H | N |  |
|---|---|---|---|---|
| Found | 64.67 | 11.26 | 17.57 | % |
| Required for $C_{13}H_{27}N_3O$ | 64.69 | 11.27 | 17.41 | % |

EXAMPLE 4

A mixture of 6.9 parts by weight of cyclohexyl isocyanate, 9.2 parts by weight of 2(2′,2′,6′,6′-tetramethylpiperidinyl-4)ethylamine, 100 parts by volume of benzene and a trace of diazobiscyclooctane was heated at reflux for 24 hours. The benzene was then removed by distillation under reduced pressure and the residual oil was treated with water (400 parts by volume) to give a white solid. This was collected by filtration, dried and purified by recrystallisation from ethyl acetate (150 parts by volume) to give N-cyclohexyl-N′-[2(2′,2′,6′,-6′-tetramethylpiperidinyl-4′)ethyl]urea, melting at 111°C. and having the following elemental analysis by weight:

| | C | H | N | |
|---|---|---|---|---|
| Found | 69.90 | 11.32 | 13.59 | % |
| Required for $C_{18}H_{35}N_3O$ | 69.86 | 11.40 | 13.58 | % |

EXAMPLE 5

A mixture of 6.6 parts by weight of phenyl isocyanate, 9.2 parts by weight of 2(2',2',6',6'-tetramethylpiperidinyl-4')ethylamine and 100 parts by volume of benzene was heated at reflux for 18 hours. The benzene was then stripped off by distillation under reduced pressure to give a white solid which was recrystallised from 100 parts by volume of ethyl acetate to give N-phenyl-N'-[2(2',2',6',6'-tetramethylpiperidinyl-4')ethyl]urea, melting at 151°–2°C. and having the following elemental analysis by weight:

| | C | H | N | |
|---|---|---|---|---|
| Found | 71.40 | 9.7 | 13.56 | % |
| Required for $C_{18}H_{29}N_3O$ | 71.25 | 9.63 | 13.85 | % |

EXAMPLE 6

A mixture of 3.6 parts by weight hexamethylene diisocyanate, 11 parts by weight of 2-(2',2',6',6'-tetramethylpiperidinyl-4')ethylamine and 100 parts by volume of petroleum ether (boiling range 60°–80°C.) was heated at reflux for 24 hours in the presence of a trace of diazobiscyclooctane. The resulting solid was collected by filtration and purified by continuous extraction with ethyl acetate, to give on drying 10.5 parts by weight (82% of theory yield of 1,6-Di[2'-(2'',2'',6'λ',6''-tetramethylpiperidinyl-4'')ethylureido]hexane, melting at 135°C. and having the following elemental analysis by weight:

| | C | H | N | |
|---|---|---|---|---|
| Found | 67.04 | 11.08 | 15.77 | % |
| Required for $C_{30}H_{60}N_6O_2$ | 67.11 | 11.27 | 15.66 | % |

EXAMPLE 7

A mixture of 6.25 parts by weight of Di(4-isocyanatophenyl)methane, 9.2 parts by weight of 2(2',2',6',6'-tetramethylpiperidinyl-4')ethylamine and 200 parts by volume of benzene was heated to reflux for 24 hours. The resulting white solid was collected by filtration and purified by continuous extraction by ethylacetate to give p,p'-Di[2-(2',2',6',6'-tetramethylpiperidinyl-4')ethylureido]diphenylmethane, melting at 208°–9°C. and having the following elemental analysis by weight:

| | C | H | N | |
|---|---|---|---|---|
| Found | 71.75 | 9.37 | 13.73 | % |
| Required for $C_{37}H_{58}N_6O_2$ | 71.80 | 9.45 | 13.58 | % |

EXAMPLE 8

43 Parts by volume of a 12½% w/v solution of phosgene in toluene was added dropwise with stirring at 10°–20°C. over 15 minutes to a solution of 36.8 parts by weight of 2-(2',2',6',6'-tetramethylpiperidinyl-4')ethylamine in 200 parts by volume of toluene.

The resulting suspension was stirred at room temperature for four hours, then heated to reflux for a further one hour.

A white solid was collected by filtration, this was dissolved in water (100 parts by volume) and the solution basified to pH 14 by the addition of sodium hydroxide. A colourless oil was precipitated, this was extracted with diethyl ether (4 × 50 parts by volume), the ether was dried over magnesium sulphate and removed by distillation under reduced pressure to give N,N'-Di[2-(2',2',6',6'-tetramethylpiperidinyl-4')ethyl]urea, melting at 75°C. and having the following elemental analysis by weight:

| | C | H | N | |
|---|---|---|---|---|
| Found | 69.95 | 11.93 | 14.40 | % |
| Required for $C_{23}H_{46}N_4O$ | 70.00 | 11.75 | 14.20 | % |

EXAMPLE 9

A solution of 9.2 parts by weight of 2-(2',2',6',6'-tetramethylpiperidinyl-4')ethylamine in 20 parts by volume of benzene was added dropwise with stirring over 15 minutes to a solution of 3.9 parts by weight of acetyl chloride in 80 parts by volume of benzene.

The resulting suspension was heated to reflux for two hours, then cooled and the solid filtered. This solid was dissolved in 50 parts by volume of water which was then basified to pH 14 by the addition of sodium hydroxide. The precipitated oil was extracted with diethyl ether (5 × 30 parts by volume), the combined ether extracts were dried over magnesium sulphate, and the ether distilled off.

By distillation of the residual oil there was obtained N-acetyl-2-(2',2',6',6'-tetramethylpiperidinyl-4') ethylamine, boiling at 156°–60°C/0.6 mm Hg and having the following elemental analysis by weight:

| | C | H | N | |
|---|---|---|---|---|
| Found | 68.69 | 11.31 | 12.24 | % |
| Required for $C_{13}H_{26}N_2O$ | 68.98 | 11.58 | 12.38 | % |

EXAMPLE 10

A solution of 9.2 parts by weight of 2-(2',2',6',6'-tetramethylpiperidinyl-4')ethylamine in 20 parts by volume of benzene was added to a solution of 4.5 parts by weight of n-butyryl chloride in 80 parts by volume of benzene over 15 minutes with stirring. The suspension was refluxed for two hours and worked up as described in Example 9.

Thus N-butyryl-2(2',2',6',6'-tetramethylpiperidinyl-4')ethylamine was obtained, boiling at 160°C/0.7 mm Hg, and having the following elemental analysis by weight:

| | C | H | N | |
|---|---|---|---|---|
| Found | 70.56 | 11.64 | 11.04 | % |
| Required for $C_{15}H_{30}N_2O$ | 70.82 | 11.89 | 11.01 | % |

EXAMPLE 11

A solution of 9.2 parts by weight of 2-(2',2',6',6'-tetramethylpiperidinyl-4')ethylamine in 20 parts by volume of benzene were added with stirring to a solution of 8.1 parts by weight of n-octanoyl chloride in 80 parts by volume of benzene and subsequently worked-up as described in Example 9. There was thus obtained N-octanoyl-2-(2',2',6',6'-tetramethylpiperidinyl-4')ethylamine, boiling at 188°–92°C/0.8 mm Hg and having the following elemental analysis by weight:

|  | C | H | N |  |
|---|---|---|---|---|
| Found | 73.17 | 12.16 | 8.68 | % |
| Required for $C_{19}H_{38}N_2O$ | 73.49 | 12.33 | 9.02 | % |

EXAMPLE 12

A solution of 18.4 parts by weight of 2-(2',2',6',6'-tetramethylpiperidinyl-4')ethylamine in 50 parts by volume of benzene was added with stirring to a solution of 21.8 parts by weight of n-dodecanoyl chloride in 200 parts by volume of benzene over 30 minutes. The reaction procedure was then continued as described in Example 9 to give N-dodecanoyl-2-(2',2',6',6'-tetramethylpiperidinyl-4') ethylamine, boiling at 208°–12°C/0.6 mm Hg, and having the following elemental analysis by weight:

|  | C | H | N |  |
|---|---|---|---|---|
| Found | 73.37 | 12.65 | 7.46 | % |
| Required for $C_{23}H_{46}N_2O$ | 75.35 | 12.65 | 7.64 | % |

EXAMPLE 13

A solution of 9.2 parts by weight of 2-(2',2',6',6'-tetramethylpiperidinyl-4')ethylamine in 20 parts by volume of benzene was added with stirring over 30 minutes to a solution of 7.0 parts by weight of benzoyl chloride in 80 parts by volume of benzene. The resulting suspension was heated to reflux for two hours, cooled, and the solid collected by filtration. The solid was dissolved in 100 parts by volume of water which was basified to pH 14 by the addition of sodium hydroxide. The precipitated oil was extracted with diethyl ether (6 × 30 parts by volume) and the combined extracts were dried over magnesium sulphate. A white solid was obtained on removal of the ether by distillation, which by recrystallisation from 100 parts by volume of petroleum ether (60°–80°C. boiling range) gave pure N-benzoyl-2-(2',2',6',6'-tetramethylpiperidinyl-4') ethylamine, melting at 101°–2°C, and having the following elemental analysis by weight:

|  | C | H | N |  |
|---|---|---|---|---|
| Found | 74.68 | 9.62 | 9.44 | % |
| Required for $C_{18}H_{28}N_2O$ | 74.96 | 9.78 | 9.71 | % |

EXAMPLE 14

A mixture of 11.4 parts by weight of ethyl(2,2,6,6-tetramethylpiperidinyl-4)acetate, 9.2 parts by weight of 2-(2',2',6',6'-tetramethylpiperidinyl-4)ethylamine and 2.7 parts by weight of sodium methoxide were heated at 160°C. for one hour with stirring. During this time ethyl alcohol was allowed to distil from the reaction vessel. The mixture was finally heated at 160°C./12 mm Hg for 15 minutes, then cooled and dissolved in 100 parts by volume diethyl ether. The ether extract was washed with water (4 × 20 parts by volume), dried over magnesium sulphate and the ether finally removed by distillation to give N-[(2'',2''', 6'',6'''-tetramethylpiperidinyl-4'')acetyl]-2-(2',2',6',6'-tetramethylpiperidinyl-4')ethylamine, as a pale green highly viscous oil having the following elemental analysis by weight:

|  | C | H | N |  |
|---|---|---|---|---|
| Found | 72.48 | 11.73 | 11.34 | % |
| Required for $C_{22}H_{43}N_3O$ | 72.28 | 11.85 | 11.49 | % |

EXAMPLE 15

A solution of 9.9 parts by weight of 2-(1',2',2',6',6'-pentamethylpiperidinyl-4')ethylamine in 20 parts by weight of benzene was added with stirring to a solution of 3.9 parts by weight of acetyl chloride in 80 parts by weight of benzene. The resulting suspension was then treated as described in Example 9 to give 8.3 parts by weight (68% of theory yield) of N-acetyl-2-(1',2',2',6',6'-pentamethylpiperidinyl-4')ethylamine, boiling at 158°–60°C./0.6 mm Hg, and having the following elemental analysis by weight:

|  | C | H | N |  |
|---|---|---|---|---|
| Found | 70.19 | 11.96 | 11.83 | % |
| Required for $C_{14}H_{28}N_2O$ | 69.95 | 11.74 | 11.65 | % |

EXAMPLE 16

A solution of 9.9 parts by weight of 2-(1',2',2',6',6'-pentamethylpiperidinyl-4')ethylamine in 20 parts by volume of benzene were added to a solution of 4.5 parts by weight of n-butyryl chloride in 80 parts by volume of benzene and worked up as described in Example 9.

In this way, N-butyryl-2-(1',2',2', 6',6'-pentamethylpiperidinyl-4)ethylamine, boiling at 166°–8°C./0.2 mm Hg. and having the following elemental analysis by weight was obtained:

|  | C | H | N |  |
|---|---|---|---|---|
| Found | 71.84 | 11.92 | 10.35 | % |
| Required for $C_{16}H_{32}N_2O$ | 71.59 | 12.02 | 10.44 | % |

EXAMPLE 17

A solution of 9.9 parts by weight of 2-(1',2',2',6',6'-pentamethylpiperidinyl-4')ethylamine in 20 parts by volume of benzene was added with stirring over 30 minutes to a solution of seven parts by weight of benzoyl chloride in 80 parts by weight of benzene. The suspension was then heated to reflux for two hours, the benzene was then decanted from the flask and the residual gum was dissolved in 200 parts by volume of water. This was basified to pH 14 by the addition of sodium hydroxide and the white solid precipitate was collected by filtration, dried and purified by recrystallisation from 50 parts by volume of cyclohexane to give ten parts by weight (67% of theory yield) of N-benzoyl-2-(1',2',2',6',6'-pentamethylpiperidinyl-4')ethylamine, melting at 107°C. and having the following elemental analysis by weight:

|  | C | H | N |  |
|---|---|---|---|---|
| Found | 75.72 | 10.05 | 9.50 | % |
| Required for $C_{19}H_{30}N_2O$ | 75.45 | 10.00 | 9.26 | % |

EXAMPLE 18

A solution of 6.6 parts by weight of phenylisocyanate, 9.9 parts by weight of 2-(1',2',2',6',6'-pentamethylpiperidinyl-4')ethylamine and petroleum ether (boiling range 80°–100°C.), containing a trace of diazobiscyclooctane, was heated at reflux for two hours, the resulting solid precipitate was collected by filtration and recrystallised from 150 parts by volume of ethyl acetate to give N-phenyl-N'-[2-(1',2',2',6',6'-pentamethylpiperidinyl-4')ethyl]urea, melting at 143°–4°C. and having the following elemental analysis by weight:

|  | C | H | N |  |
|---|---|---|---|---|
| Found | 72.23 | 9.91 | 13.22 | % |
| Required for $C_{19}H_{31}N_3O$ | 71.88 | 9.84 | 13.24 | % |

EXAMPLES 19 to 28

38 parts of polypropylene were homogenised with 0.076 part of n-octadecyl-$\beta$-(4'-hydroxy-3',5'-t-butylphenyl) propionate in a kneading machine at a temperature of 200°C over a period of 3 minutes. 0.19 part of the product of Example 1 was then added and homogenisation continued for another 7 minutes.

The homogenised mixture was removed from the kneader and pressed to a thickness of 2–3 mm in a press at a temperature of 200°C. 9 parts of the polypropylene mixture were then charged into a press in which the press-plates were protected by 0.1 mm thick aluminium foil. The sample was surrounded by four strips of steel skim, 0.3 mm thick, in the form of a square, acting as spacers between the aluminium foils. The press was closed and for 2 minutes no pressure was applied. The pressure was then increased over 2 minutes up to a maximum of 12 tons and this pressure held for a further 2 minutes, the temperature being 260°C.

The pressure was released and the material (0.3 mm thick) was cooled immediately under running water.

2.2 parts of this material was cut in the form of a square and recharged to the press. Conditions were as for the previous pressure except that 0.1 mm thick steel skim was used for spacing between the aluminium foils. The press was closed and no pressure was applied for 2 minutes. Over another 2 minutes the pressure was increased to 8 tons, the press temperature being 260°C. This pressure was maintained for 2 minutes and then the pressure released. The "sandwich" of the 0.1 mm thick polypropylene foil and aluminium foils was then removed and tempered immediately for 1 hour in a circulating-air oven maintained at 150°C. The "sandwich" was then quenched in running cold water and the aluminium foils were peeled from the inner polypropylene foil and the skim spacers removed.

A section measuring 44 × 100 mm was separated from the 0.1 mm tempered polypropylene foil and exposed to light irradiation in a fademeter device consisting of a circular bank of 28 alternate sunlight and blacklight lamps. The sunlight lamps were 2 feet long, 20-watt fluorescent lamps characterised by a peak emission of 3000 Angstrom units; the blacklight lamps were 2 feet long, 20-watt ultraviolet lamps characterised by a peak emission of 3500 Angstron units. The sample was rotated concentrically within the bank of lamps so that the radiation therefrom was uniformly distributed over the section under test.

The exposed sample was examined periodically and the time (T) at which the sample reached 50% of the initial elongation at break was noted.

The time (Tc) for the elongation of a control sample (not containing the product of Example 1) to decrease to 50% of the initial elongation was then determined.

The performance of the compound of formula I as a light stabiliser could then be assessed by determining the factor T/Tc.

The results obtained including those relating to other compounds of formula I are summarised in the following Table.

| | | FACTOR T/TC |
|---|---|---|
| Ex. | Product | Time to 50% of Initial Elongation at Break / Time to 50% of Initial Elongation at Break for CONTROL |
| 19 | N-Benzoyl-2-(2',2',6',6'-tetramethylpiperidinyl-4')ethylamine | 3.5 |
| 20 | N-Phenyl-N'-[2(2',2',6',6'-tetramethylpiperidinyl-4')ethyl]urea | 7.3 |
| 21 | N-Cyclohexyl-N'-[2-(2',2',6',6'-tetramethylpiperidinyl-4')ethyl]urea | 6.3 |
| 22 | N-Octanoyl-2-(2',2',6',6'-tetramethylpiperidinyl-4')ethylamine | 8.3 |
| 23 | N-Acetyl-2-(2',2',6',6'-tetramethylpiperidinyl-4')ethylamine | >6.0 i.e. 6.2 |
| 24 | N-Butyryl-2-(2',2',6',6'-tetramethylpiperidinyl-4')ethylamine | >5.7 i.e. 6.0 |
| 25 | N-[(2'',2'',6'',6''-Tetramethylpiperidinyl-4''')acetyl]-2-(2',2',6',6'-tetramethylpiperidinyl-4')ethylamine | 6.4 |
| 26 | 2-(2',2',6',6'-Tetramethylpiperidinyl-4')ethylamine | >9.3 i.e. 9.5 |
| 27 | N-methyl-n'-[2(2',2',6',6'-tetramethylpiperidinyl-4')ethyl]urea | >8.8 |
| 28 | N-Phenyl-[2-(2',2',6',6'-tetramethylpiperidinyl-4')ethyl]urethane | 6.0 |

EXAMPLE 29

A solution of 9.9 parts by weight of 2(1',2',2',6',6'-pentamethylpiperidinyl-4')ethylamine in 20 parts by volume of dry benzene was added, with stirring, to a solution of 8.1 parts by weight of n-octanoyl chloride in 80 parts by volume of dry benzene over 20 minutes. The resulting suspension was stirred at room temperature for 15 minutes, then heated to reflux for a further 2 hours. The suspension was then cooled and the solid was filtered and worked up as for Example 9.

Thus pure N-octanoyl-[2(1',2',6',6'-pentamethylpiperidinyl-4)ethylamine] was obtained, boiling at 196°–8°C/0.6 mm Hg. and having the following elemental analysis by weight:

|  | C | H | N |
|---|---|---|---|
| Found: | 73.96 | 12.42 | 8.39 % |
| Required for: $C_{20}H_{40}N_2O$ | 74.02 | 12.42 | 8.63 % |

EXAMPLE 30

A solution of 19.8 parts by weight of 2-(1',2',2',6',6'-pentamethylpiperidinyl-4')ethylamine in 50 parts by weight of dry benzene was added with stirring to a solution of 21.8 parts by weight of n-dodecanoyl chloride in 200 parts by volume of dry benzene over 20 minutes. The suspension was stirred at room temperature for 15 minutes, then heated to reflux for 4 hours, and finally worked up in the manner described in Example 9.

Thus 21.0 parts by weight (55% of theory yield) of N-n-dodecanoyl[2-(1',2',2',6',6'-pentamethylpiperidinyl-4')ethylamine] were obtained, boiling at 222°–4°C/0.6 mm Hg, and having the following elemental analysis by weight:

|  | C | H | N |
|---|---|---|---|
| Found: | 75.83 | 12.56 | 7.38 % |
| Required for: $C_{24}H_{48}N_2O$ | 75.73 | 12.71 | 7.36 % |

EXAMPLE 31

A solution of 9.6 parts by weight of sebacoyl chloride in 25 parts by volume of dry benzene was added over 15 minutes, with stirring, to a solution of 19.2 parts by weight of 2-(1',2',2',6',6'-pentamethylpiperidinyl-4')ethylamine in 75 parts by volume of dry benzene. The resulting suspension was heated at reflux for 24 hours, then cooled and the solid was collected by filtration. This was dissolved in 100 parts by volume of water, and the water made strongly basic by the addition of 46% aqueous sodium hydroxide, to give an oil which was extracted into ether (6 × 50 parts by volume). The combined ether extracts were dried over magnesium sulphate, and the ether removed by distillation under reduced pressure to give a white solid. This was purified by recrystallisation from ethyl acetate to give N,N'-Di[2(1',2',2',6',6'-pentamethylpiperidinyl-4')ethyl] sebacamide, melting at 122°–3°C and having the following elemental analysis by weight:

|  | C | H | N |
|---|---|---|---|
| Found: | 72.86 | 11.77 | 9.78 % |
| Required for: $C_{34}H_{66}N_4O_2$ | 72.55 | 11.82 | 9.95 % |

EXAMPLE 32

A solution of 6.2 parts by weight of succinyl chloride in 25 parts by volume of dry benzene was added dropwise over 15 minutes with stirring to a solution of 19.8 parts by weight of 2(1',2',2',6',6'-pentamethylpiperidinyl-4')ethylamine in 75 parts by volume of dry benzene.

The suspension was heated to reflux for 2 hours and then cooled, the solid was filtered and worked up in the manner described in Example 31 to give N,N'-Di[2-(1',2',2',6',6'pentamethylpiperidinyl-4')ethyl]succinamide, melting at 171°–2°C., and having the following elemental analysis by weight:

|  | C | H | N |
|---|---|---|---|
| Found: | 69.97 | 11.31 | 11.65 % |
| Required for: $C_{28}H_{54}N_4O_2$ | 70.25 | 11.37 | 11.70 % |

EXAMPLE 33

A solution of 9.9 parts by weight of 2-(1',2',2',6',6'-pentamethylpiperidinyl-4') ethylamine and 6.9 parts by weight of cyclohexyl isocyanate in 100 parts by volume of dry benzene containing a trace of diazobicyclooctane was heated at reflux for 24 hours. The benzene was removed by distillation under reduced pressure and the solid residue was recrystallised from ethylacetate to give 9.3 parts by weight (57% of theory yield) of N-cyclohexyl-N'-[2-(1',2',2',6',6'-pentamethylpiperidinyl-4')ethyl]urea, melting at 154°–5°C and having the following elemental analysis by weight:

|  | C | H | N |
|---|---|---|---|
| Found: | 70.79 | 11.67 | 12.70 % |
| Required for: $C_{19}H_{37}N_3O$ | 70.54 | 11.53 | 12.99 % |

EXAMPLE 34

A solution of 11.8 parts by weight of 2-(1',2',2',6',6'-pentamethylpiperidinyl-4')ethylamine and 3.6 parts by weight of 1,6-diisocyanatohexane in 150 parts by volume of petroleum ether (60°–80°C boiling range) containing a trace of diazabicyclooctane, was heated at reflux for 2 hours.

The suspension was cooled, and the resulting solid collected by filtration. Recrystallisation from ethyl acetate gave 8.2 parts by weight (58% of theory yield) of pure 1,6-Di[2'(1'',2'',2'',6'',6''-pentamethylpiperidinyl-4'')ethylureido]hexane, melting at 198°–9°C, and having the following elemental analysis by weight:

|  | C | H | N |
|---|---|---|---|
| Found: | 67.82 | 11.19 | 14.80 |
| Required for: $C_{32}H_{64}N_6O_2$ | 68.10 | 11.35 | 14.90 |

EXAMPLE 35

A solution of 9.9 parts by weight of 2-(1',2',2',6',6'-pentamethylpiperidinyl-4')ethylamine and 3.1 parts by weight of methylisocyanate in 100 parts by volume of petroleum ether (boiling range 60°–80°C) was heated at reflux for 24 hours. The petrol was then removed by distillation under reduced pressure and the residue recrystallised from ethyl acetate to give pure N-methyl-N'-[2(1',2',2',6',6'-pentamethylpiperidinyl-4')ethyl- ]urea, melting at 87°–8°C, and having the following elemental analysis by weight:

|  | C | H | N |
|---|---|---|---|
| Found: | 65.94 | 11.40 | 16.21 % |
| Required for: $C_{14}H_{29}N_3O$ | 65.84 | 11.44 | 16.45 % |

EXAMPLE 36

A solution of 8.6 parts by weight of thiodipropionyl chloride in 50 parts by volume of benzene was added dropwise with stirring over 20 minutes to a solution of 2(2',2',6',6'-tetramethyl piperidinyl-4')ethylamine in 200 parts by volume of benzene. The resulting suspension was heated at reflux for a further 2 hours, and the solid then collected by filtration, dissolved in 500 parts by volume of water and basified to pH 14 by the addition of 40% sodium hydroxide solution. The precipitated oil was extracted with chloroform (6 × 50 parts by volume), the bulked extracts were dried and the chloroform removed by distillation under reduced pressure. The residue was purified by distillation to give N,N'-Di[2(2',2',6',6'-tetramethylpiperidinyl-4')ethyl]thiodipropionamide boiling at 280°/0.6 mm Hg and having the following elemental analysis by weight:

|  | C | H | N |
|---|---|---|---|
| Found | 66.09 | 10.51 | 10.85 % |
| Required for $C_{28}H_{54}N_4O_2S$ | 65.84 | 10.66 | 10.97 % |

EXAMPLE 37

A solution of 9.9 parts by weight of 2(1',2',2',6',6'-pentamethylpiperidinyl-4')ethylamine in 50 parts by volume of cyclohexane was added dropwise to a solution of 7.7 parts by weight of phenylacetyl chloride in 100 parts by volume of cyclohexane over 30 mins. The resulting suspension was heated at reflux for 2 hours and worked up as in Example 9 to give N[2(1',2',2',6',6'-pentamethylpiperidinyl-4')ethyl]phenylacetamide, boiling at 185°–8°/0.3 mm Hg and having the following elemental analysis by weight:

|  | C | H | N |
|---|---|---|---|
| Found | 75.78 | 10.07 | 8.79 % |
| Required for $C_{20}H_{32}N_2O$ | 75.90 | 10.19 | 8.85 % |

EXAMPLE 38

A solution of 9.9 parts by weight of 2(1',2',2',6',6'-pentamethylpiperidinyl-4)ethylamine in 50 parts by volume of cyclohexane was added dropwise to a solution of 5.3 parts by weight isobutyryl chloride in 100 parts by volume of cyclohexane. The suspension was heated to reflux for 2 hours and worked up as in Example 9 to give N[2(1',2',2',6',6'-pentamethylpiperidinyl-4')ethyl]isobutyramide, boiling at 150°–5°/0.2 mm and having the following elemental analysis by weight:

|  | C | H | N |
|---|---|---|---|
| Found | 71.77 | 11.72 | 10.22 % |
| Required for $C_{16}H_{32}N_2O$ | 71.59 | 12.02 | 10.44 % |

EXAMPLE 39

A solution of 6.1 parts by weight of fumaryl chloride in 50 parts by volume of cyclohexane was added dropwise to a solution of 15.8 parts by weight of 2(1',2',-2'6',6'-pentamethylpiperidinyl-4')ethylamine in 100 parts by volume of cyclohexane, over 30 mins. at room temperature. The resulting solid was collected by filtration and dissolved in 500 parts by volume of water. The solution was basified to pH 14 by the addition of 40% sodium hydroxide solution. The precipitate was collected by filtration and purified by recrystallisation from ethylacetate to give N,N'-Di[2(1',2',2',6',6'-pentamethylpiperidinyl-4')ethyl]fumaramide, melting at 250°–3° and having the following elemental analysis by weight:

|  | C | H | N |
|---|---|---|---|
| Found | 70.72 | 10.89 | 11.46 % |
| Required for $C_{28}H_{52}N_4O_2$ | 70.54 | 10.99 | 11.75 % |

EXAMPLE 40

A solution of 9.9 parts by weight 2(1',2',2',6',6'-pentamethylpiperidinyl-4')ethylamine and 6.7 parts by weight of n-hexyisocyanate in 100 parts by volume of petroleum ether (boiling range 60°–80°) was heated at reflux for 24 hours. The solvent was removed by evaporation under reduced pressure and the residual oil distilled to give 8.0 parts by weight (50% of theory yield) of N-(n-hexyl)-N'[2(1',2',2',6',6'-pentamethylpiperidinyl-4')ethyl]urea, boiling at 198°–204°/0.2 mm Hg, and having the following elemental analysis by weight:

|  | C | H | N |
|---|---|---|---|
| Found | 70.60 | 12.08 | 12.81 % |
| Required for $C_{19}H_{39}N_3O$ | 70.10 | 12.08 | 12.91 % |

EXAMPLE 41

A solution of 9.9 parts by weight of 2(1',2',2',6',6'-pentamethylpiperidinyl-4')ethylamine and 14.8 parts by weight of n-Octadecylisocyanate in 150 parts by volume of cyclohexane was heated at reflux for 48 hours. The solvent was removed by distillation and the residual solid recrystallised from methyl alcohol to give 13.2 parts by weight (51% of theory yield) of N-(n-octadecyl)-N'-[2(1',2',2',6',6'-pentamethylpiperidinyl-4')ethyl]urea, melting at 67°–9°, and having the following elemental analysis by weight:

|  | C | H | N |
|---|---|---|---|
| Found | 75.61 | 12.48 | 8.25 % |
| Required for $C_{31}H_{63}N_3O$ | 75.39 | 12.86 | 8.51 % |

EXAMPLE 42

Ethylene oxide gas was bubbled through a stirred solution of 19.8 parts by weight 2(1',2',2',6',6'-pentamethylpiperidinyl-4)ethyl amine in 100 parts by volume of water at 10°–15° until 4.4 parts by weight had been absorbed. The resulting solution was distilled to give N-(2''-hydroxyethyl)-[2(1',2',2',6',6'-pentamethylpiperidinyl-4')]ethyl-amine boiling at 168°–72°/1.5 mm Hg, and having the following elemental analysis by weight:

|  | C | H | N |
|---|---|---|---|
| Found | 69.36 | 12.36 | 11.39 % |
| Required for $C_{14}H_{30}N_2O$ | 69.37 | 12.47 | 11.56 % |

EXAMPLE 43

Ethylene oxide gas was bubbled through a stirred solution of 18.4 parts by weight 2(2',2',6',6'-tetramethylpiperidinyl-4')ethylamine in 100 parts by volume of water at 15°–20° until a total of 15 parts by weight had been absorbed, the resulting solution was distilled to give 15 parts by weight (55% of theory yield) of N,N-Di(2''-hydroxyethyl)[2(2',2',6',6'-tetramethylpiperidinyl-4')]ethylamine, boiling at 160°–2°/0.2 mm Hg and having the following elemental analysis by weight:

|  | C | H | N |
|---|---|---|---|
| Found | 65.90 | 11.62 | 9.99 % |
| Required for $C_{15}H_{32}N_2O_2$ | 66.13 | 11.84 | 10.28 % |

EXAMPLE 44

Ethylene oxide was bubbled through a solution of 19.8 parts by weight 2(1',2',2',6',6'-pentamethylpiperidinyl-4')ethylamine in 100 parts by volume of water at 25° until 9.0 parts by weight had been absorbed, the solution was distilled to give N,N-Di(2''-hydroxyethyl)[2''(1', 2',2',6',6'-pentamethylpiperidinyl-4')]ethylamine, boiling at 158°–62°/0.2 mm Hg, and having the following elemental analysis by weight:

|  | C | H | N |
|---|---|---|---|
| Found | 67.32 | 11.83 | 9.85 % |
| Required for $C_{16}H_{34}N_2O_2$ | 67.09 | 11.96 | 9.78 % |

EXAMPLE 45

14.4 Parts by weight of ethylchloroformate were added to a stirred mixture of 22.0 parts by weight 2(2',2',6',6'-tetramethylpiperidinyl-4')ethylamine, 5.0 parts by weight of potassium carbonate, 30 parts by volume of water and 10 parts by volume of cyclohexane at 15°–20° over 20 minutes. The suspension was then stirred at room temperature for 1 hour, and then extracted with ether(6 × 25 parts by volume), the ether extracts were bulked, dried over magnesium sulphate and evaporated under reduced pressure. The residual oil was purified by distillation to give ethyl(2,2,6,6-tetramethylpiperidinyl-4)carbamate, boiling at 115°/0.5 mm Hg and having the following elemental analysis by weight:

|  | C | H | N |
|---|---|---|---|
| Found | 65.29 | 10.76 | 10.74 % |
| Required for $C_{11}H_{23}N_2O_2$ | 65.59 | 11.01 | 10.93 % |

EXAMPLE 46

19.8 Parts by weight of 2(1',2',2',6',6'-pentamethylpiperidinyl-4')ethylamine were added dropwise over 10 minutes to a stirred mixture of 4.8 parts by weight carbon disulphide and 13 parts by volume water and the resulting suspension was stirred at room temperature for a further 2 hours. 4.5 parts by weight of 50% sodium hydroxide solution were then added and the suspension was heated at reflux for 3 hours.

After cooling the solid was collected by filtration and extracted with boiling ethyl alcohol (500 parts by volume), the ethyl alcohol extract was evaporated under reduced pressure and the residual oil treated with water to give N,N'-Bis[2(1',2',2',6',6'-pentamethylpiperidinyl-4')ethyl]thiourea as the monohydrate, melting at 118°–20°, and having the following elemental analysis by weight:

|  | C | H | N |
|---|---|---|---|
| Found | 65.88 | 10.98 | 12.0 % |
| Required for $C_{25}H_{52}N_4OS$ | 65.75 | 11.45 | 12.27 % |

EXAMPLE 47

A solution of 35.6 parts by weight of (2,2,6,6-tetramethylpiperidinylidene-4)acetonitrile (see Example 1) and 17.1 parts by weight of benzylbromide in 100 parts by volume of toluene was heated at reflux for 48 hours, the resulting precipitate was removed by filtration and the solution evaporated under reduced pressure, the residual oil was purified by distillation (b. 160°–4°10.7mm Hg.), dissolved in 60 parts by volume of saturated methyl alcohol/ammonia solution and hydrogenated at room temperature and a pressure of 20 atmospheres hydrogen over Raney nickel catalyst.

After removal of the catalyst, by filtration, and the solvent, by evaporation under reduced pressure, the residual oil was distilled to give 2(1'-benzyl-2',2'-6,40,6'-tetramethylpiperidinyl-4')ethylamine, boiling at 165°/0.2mm Hg, and having the following elemental analysis by weight:

|  | C | H | N |
|---|---|---|---|
| Found | 78.53 | 10.82 | 9.76 % |
| Required for $C_{18}H_{30}N_2$ | 78.78 | 11.02 | 10.21 % |

EXAMPLE 48

A solution of 17.8 parts by weight of (2,2,6,6-tetramethylpiperidinylidene-4)acetonitrile (See Example 1) and 50 parts by volume of styrene oxide in 50 parts by volume of n-hexanol was heated at reflux for 48 hours, then distilled to give a fraction boiling at 210°–215°/0.6 mm Hg. This was hydrogenated at 100°C/100 atm. hydrogen over Raney nickel in 100 parts by volume of saturated methyl alcohol/ammonia solution.

The product was isolated as in Example 47 to give 2[1(2′-hydroxy-2′-phenylethyl)2′,2′,6′,6′-tetramethylpiperidinyl-4′[ethylamine, boiling at 185°/0.3 mm and having the following elemental analysis by weight:

|  | C | H | N |  |
|---|---|---|---|---|
| Found | 74.59 | 10.41 | 8.39 | % |
| Required for $C_{19}H_{32}N_2O$ | 74.95 | 10.59 | 8.74 | % |

EXAMPLE 49

A solution of 11.3 parts by weight N-acetyl[2(2′,2′,6′,6′-tetramethylpiperidinyl-4′)]ethylamine (see Example 9) and 3 parts by weight of allyl bromide in 100 parts by volume of toluene was heated at reflux for 16 hours. The resulting solid was removed by filtration and the toluene evaporated off under reduced pressure. The residual oil was distilled to give N-acetyl[2(1′-allyl-2′,2′,6′,6′-tetramethylpiperidinyl-4′)]ethylamine, boiling at 161°–2°/0.4 mm Hg, and having the following elemental analysis by weight:

|  | C | H | N |
|---|---|---|---|
| Found | 72.10 | 11.15 | 10.53 |
| Required by $C_{16}H_{30}N_2O$ | 72.13 | 11.35 | 10.51 |

EXAMPLE 50

9.2 Parts by weight of 2(2′,2′,6′,6′-tetramethylpiperidinyl-4′)ethylamine were added dropwise to a solution of 9.5 parts by weight of p-toluenesulphonyl chloride in 100 parts by volume of benzene. The suspension was heated to reflux for 2 hours, cooled and the solid collected by filtration. Recrystallisation from water gave 12.0 parts by weight (64% of theory yield) of N-[2′(2″,2″,6″,6″-tetramethylpiperidinyl-4′)ethyl]toluene-4-sulphonamide, hydrochloride, melting with decomposition at 258°–65°C and having the following elemental analysis by weight:

|  | C | H | N | S |  |
|---|---|---|---|---|---|
| Found | 57.99 | 8.23 | 7.63 | 8.47 | % |
| Required for $C_{18}H_{31}ClN_2O_2S$ | 57.60 | 8.27 | 7.47 | 8.54 | % |

EXAMPLE 51

4.0 Parts by weight of sodium hydride (60% in oil) and 15.5 parts by weight of 2,2,6,6-tetramethylpiperidin-4-one in 125 parts by volume of cyclohexane (dry) were stirred together at room temperature. To this mixture was added 23.3 parts by weight of (α-n-butyl)-diethylphosphonoacetonitrile in 25 parts by volume of cyclohexane over 30 minutes. The suspension was stirred at room temperature for 1 hour, then heated at reflux for 2 hours and 100 parts by volume of water were added to the cooled suspension. The cyclohexane was separated, dried over magnesium sulphate, and evaporated off under reduced pressure. The residual oil was distilled to give 9.7 parts by weight (40% of theory yield) of α-n-butyl(2,2,6,6-tetramethylpiperidinyl-4)acetonitrile boiling at 150°–4°/12 mm Hg and identified by p.m.r. spectroscopy.

This was then hydrogenated at 100°C/100 atmospheres of hydrogen over Raney nickel catalyst in 100 parts by volume of saturated methyl alcohol/ammonia solution. The product was isolated as in Example 47 to give 2-(n-butyl)2(2′,2′,6′,6′-tetramethylpiperidinyl-4′)ethylamine boiling at 104°/0.3 mm Hg, and having the following elemental analysis by weight:

|  | C | H | N |
|---|---|---|---|
| Found | 74.37 | 13.00 | 12.45 |
| Required for $C_{15}H_{32}N_2$ | 74.93 | 13.42 | 11.65 |

EXAMPLE 52

A solution of 9.25 parts by weight 2-(2′,2′,6′,6′-tetramethylpiperidinyl-4′)ethyl alcohol and 6.6 parts by weight of phenyl isocyanate in 100 parts by volume of petroleum ether (boiling range 60°–80°) was heated at reflux for 24 hours. The solvent was removed by evaporation under reduced pressure and the residue recrystallised from petroleum ether (boiling range 60°–80°) to give 8.3 parts by weight (55% of theory yield) of N-phenyl[2(2′,2′,6′,6′-tetramethylpiperidinyl-4′)-ethyl]urethane, melting at 91°–2°C and having the following elemental analysis by weight:

|  | C | H | N |
|---|---|---|---|
| Found | 70.79 | 11.67 | 12.70 % |
| Required for $C_{18}H_{28}N_2O_2$ | 70.54 | 11.53 | 12.99 % |

EXAMPLE 53

A solution of 7.4 parts by weight of 2(2′,2′,6′,6′-tetramethylpiperidinyl-4′)ethyl alcohol and 2.3 parts by weight of methyl isocyanate in 100 parts by volume of cyclohexane was heated at reflux for 24 hours. The solvent was removed by evaporation under reduced pressure and the residual oil distilled to give 4.9 parts by weight (51% of theory yield) of N-methyl[2(2′,2′,6′,6′-tetramethylpiperidinyl-4′)ethyl]urethane, boiling at 124°–8°/0.5 mm Hg, and having the following elemental analysis by weight:

|  | C | H | N |
|---|---|---|---|
| Found | 64.66 | 10.70 | 11.32 |
| Required for $C_{13}H_{26}N_2O_2$ | 64.43 | 10.81 | 11.56 |

EXAMPLE 54

A solution of 9.3 parts by weight of 2(2′,2′,6′,6′-tetramethylpiperidinyl-4′)ethyl alcohol and 6.2 by weight of cyclohexyl isocyanate was heated to reflux for 24 hours. The product was isolated as in Example 53 to give 9.8 parts by weight (63% of theory yield) of N-Cyclohexyl[2(2',2',6',6'-tetramethylpiperidinyl-4')ethyl]urethane, boiling at 186°–90°/2.0 mm Hg, and having the following elemental analysis by weight:

|  | C | H | N |
|---|---|---|---|
| Found | 69.73 | 11.39 | 8.86 % |
| Required for $C_{18}H_{34}H_2O_2$ | 69.63 | 11.04 | 9.02 % |

EXAMPLE 55

A solution of 9.3 parts by weight of 2(2',2',6',6'-tetramethylpiperidinyl-4')ethyl alcohol and 3.3 parts by weight of hexamethyldiisocyanate in 100 parts by volume of cyclohexane was heated at reflux for 24 hours and worked up as in Example 53 to give N,N'-Di[2'(-2'',2'',6'',6''-tetramethylpiperidinyl-4''')ethyloxycarbonyl]hexane-1,6-diamine, boiling at 270°/0.5 mm Hg, and having the following elemental analysis by weight:

|  | C | H | N |
|---|---|---|---|
| Found | 67.05 | 10.68 | 10.65 % |
| Required for $C_{30}H_{58}N_4O_4$ | 66.87 | 10.85 | 10.40 % |

EXAMPLE 56

A solution of 7.4 parts by weight of 2(2',2',6',6'-tetramethylpiperidinyl-4')ethyl alcohol, 8.0 parts by weight of dodecanoic acid, and 0.5 parts by weight of tetra(t-butyl)titanate in 150 parts by volume of xylene was heated at reflux for 6 hours. Water was collected from the distillate in a 'Dean and Stark' apparatus. The xylene solution was then cooled, washed with sodium carbonate solution and dried over magnesium sulphate. Xylene was evaporated off under reduced pressure at 100°C and the residual oil purified by distillation to give [2(2',2',6'-6',6'-tetramethylpiperidinyl-4')ethyl]-dodecanoate, boiling at 200°/0.5 mm Hg, and having the following elemental analysis by weight:

|  | C | H | N |
|---|---|---|---|
| Found | 75.07 | 12.06 | 3.61 % |
| Required for $C_{23}H_{45}NO_2$ | 75.15 | 12.34 | 3.81 % |

EXAMPLE 57

1.6 Parts by weight of sodium hydride (60% in oil) was added to a solution of 7.4 parts by weight of 2(2',-2',6',6'-tetramethylpiperidinyl-4')ethyl alcohol in 100 parts by volume of toluene and the resulting suspension was heated at reflux for 24 hours. 7.7 Parts by weight of n-bromooctane were then added and the reflux continued for a further 24 hours.

The solid precipitate was removed by filtration and the toluene evaporated off under reduced pressure to give a residual oil which was purified by distillation giving 5.6 parts by weight (50% of theory yield) (n-octyl)-[2(2',2',6',6'-tetramethylpiperidinyl-4')e- thyl]ether, boiling at 200°/0.5 mm Hg, and having the following elemental analysis by weight:

|  | C | H | N |
|---|---|---|---|
| Found | 76.78 | 13.23 | 4.58 % |
| Required by $C_{19}H_{39}NO$ | 76.70 | 13.21 | 4.71 % |

EXAMPLE 58

A mixture of 11.4 parts by weight of ethyl(2,2,6,6-tetramethylpiperidinyl-4)acetate, 9.3 parts by weight of 2(2',2',6',6'-tetramethylpiperidinyl-4')ethyl alcohol and 0.5 parts by weight of lithium amide were heated at 180° for 1 hour during which ethyl alcohol was allowed to distil from the reaction vessel. The suspension was then cooled and poured into water and the resulting oil was extracted with ether (3 × 50 parts by volume), the bulked ether extracts were dried over magnesium sulphate and the ether evaporated off under reduced pressure. Distillation of the residual oil gave 8.3 parts by weight of [2(2',2',6',6'-tetramethyl-piperidinyl-4')ethyl] (2'',2'',6'',6''-tetramethylpiperidinyl-4'')-acetate, boiling at 180°–1°C/0.9 mm Hg, and having the following elemental analysis by weight:

|  | C | H | N |
|---|---|---|---|
| Found | 71.51 | 11.45 | 7.52 % |
| Required for $C_{22}H_{42}N_2O_2$ | 72.08 | 11.55 | 7.64 % |

EXAMPLE 59

A solution of 9.9 parts by weight of 2(1',2',2',6',6'-pentamethylpiperidinyl-4')ethylamine in 75 parts by volume of cyclohexane was added dropwise to a solution of 5.2 parts by weight of crotonyl chloride in 75 parts by volume of cyclohexane, the suspension was then heated to reflux for 1 hour and worked up as in Example 9 to give N-crotyl[2(2',2'-6',6'-tetramethyl-piperidinyl-4')]ethylamine, boiling at 160°–3°/0.25 mm Hg, melting at 79°–81°, and having the following elemental analysis by weight:

|  | C | H | N |
|---|---|---|---|
| Found | 72.63 | 11.30 | 10.82 % |
| Required for $C_{16}H_{30}N_2O$ | 72.13 | 11.35 | 10.51 % |

EXAMPLES 60 TO 62

The procedure described in Examples 19 to 28 was repeated except that the substrate used was high-density polyethylene, the kneading was carried out at 180°C. for 10 minutes and the homogenized material was compression moulded to films 0.110 mm thickness, using temperature of 210°C. for 6 minutes.

The compression moulded film under test was then exposed in a Xenotest 150 device and the time for the carbonyl content of the sample to increase to 0.1% by weight was noted.

The data obtained are set out in the following Table II

TABLE II

| Example | Light stabilizer | Time to 0.1% Carbonyl content. |
|---|---|---|
| control | 0.5% N-octadecyl-3[3,5-di-t-butyl- | 700 |
| 60 | 0.5% N-octadecyl-3[3,5-di-t-butyl-4-hydroxyphenyl]propionate. + 0.25% N-Phenyl-N'-[2(2',2',6',6'-tetramethylpiperidinyl-4')ethyl]urea | >2000 |
| 61 | 0.05% N-octadecyl-3[3,5,-di-t-butyl-4-hydroxyphenyl]propionate. + 0.25% N-(n-octanoyl)2(2',2'6'-tetramethylpiperidinyl-4')ethylamine | >2000 |
| 62 | 0.05% N-octadecyl-3[3,5-di-t-butyl-4-hydroxyphenyl]propionate + 0.25% 2(2',2',6',6'-tetramethylpiperidinyl-4')ethylamine | 1.300 |

EXAMPLES 63 TO 65

100 Parts of crystal polystyrene pellets were dry blended with 0.25 part of light stabilizer under test, and the dry blend was homogenised by extrusion. The stabilised pellets so obtained were injection moulded to form plaques 1.5 mm. thick. These plaques were exposed for 3000 hours in a "Xenotest 150" exposure unit, and any yellowing of the plaques was measured by determining the yellowness factor by means of the following equation:

$$\text{yellowness factor} = \frac{\Delta T_{(420)} - \Delta T_{(680)}}{T_{(560)}} \times 100$$

wherein the ΔT values represent the transmission loss of the sample at wavelengths of 420 mm. and 680 mm. respectively, after exposure in the Xenotest unit, and $T_{(560)}$ represents the transmission value of an unexposed sample at a wavelength of 560 mm.

The results obtained, as well as the results relating to a control experiment and other compositions of this invention are recorded in the following Table III.

TABLE III

| Example | Light stabilizer | Yellowing factor after 2000 hrs. |
|---|---|---|
| — | None | 20.2 |
| 63 | N-Phenyl-N'-[2(2',2',6',6'-tetramethylpiperidinyl-4')ethyl]urea | 9.1 |
| 69 | N(n-Octanoyl)-2(2',2',6',6'-tetramethylpiperidinyl-4')ethylamine | 7.9 |
| 65 | 2(2',2'6',6'-Tetramethylpiperidinyl-4')ethylamine | 8.9 |

EXAMPLES 66 TO 68

25 parts by weight of a polyester-based film-forming polyurethane were dissolved in 75 parts by weight of a 1:1 mixture (by volume) of dimethylformamide and acetone, and 1% by weight of light stabilizer was added. The clear and homogeneous solution was drawn out on a glass plate to a film of 400–500 μ thickness, which was then dried as follows:
at 50°C for 4 minutes
at 140°C for 6 minutes
The final thickness of the film was 80–100 μ.

The dried film samples were removed from the glass plate, mounted on white cardboard and exposed in a "Xenotest 450" exposure unit, one half of the exposed sample being covered to facilitate subsequent visual estimation of yellowing due to exposure. The sample was controlled and rated visually at intervals of 100 hours.

The data obtained are set out in the following Table IV which also includes data relating to a control experiment (no added light stabiliser) and to other experiments using stabilisers of this invention.

TABLE IV

| Example | Light stabilizer | Time to distinct yellowing | |
|---|---|---|---|
| | | Natural | Pigments |
| — | None | 200 | 200 |
| 66 | N-Phenyl-N'-[2(2',2',6',6'-tetramethylpiperidinyl-4'-)-ethyl]urea | 1000 | 800 |
| 67 | N-(n-Octanoyl)-2(2',2',6',6'-tetramethylpiperidinyl-4')-ethylamine | 800 | 800 |
| 68 | 2(2',2',6',6'-Tetramethylpiperidinyl-4')ethylamine | 600 | 600 |

EXAMPLE 69

A solution of 4.0 parts by weight of 2(1',2',2',6',6'-pentamethylpiperidinyl-4')ethylamine and 3.7 parts by weight of 1-naphthylisothiocyanate in 50 parts by volume of cyclohexane was heated at reflux for 24 hours. The cyclohexane was removed by distillation and the residue recrystallised from petroleum ether (boiling range 60–80°C) to give N-[2(1',2',2',6',6'-pentamethylpiperidinyl-4')ethyl]N'-(1''-naphyl)thiourea, melting at 107°–9°C and having the following elemental analysis by weight:

| | C | H | N | |
|---|---|---|---|---|
| Found | 71.82 | 8.77 | 10.47 | % |
| Required for $C_{23}H_{33}N_3S$ | 72.10 | 8.63 | 10.96 | % |

EXAMPLE 70

24.9 Parts by weight of n-dodecyl bromide and 36.5 parts by weight of (2,2,6,6-tetramethylpiperidinylidene-4)acetonitrile were heated together at 140°C for 6 days. The solid precipitate was removed by filtration and the liquid was distilled to give 10.5 parts by weight [1-(n-dodecyl)2,2,6,6-tetramethylpiperidinylidene-4]acetonitrile boiling at 200°–5°C./0.6mm.

This was hydrogenated and worked up as in Example 47 to give 2[1'-(n-dodecyl)-2',2',6',6'-tetramethylpiperidinyl-4']ethylamine, boiling at 190°–5°C./0.2 mm Hg and having the following elemental analysis by weight:

| | C | H | N | |
|---|---|---|---|---|
| Found | 79.45 | 13.89 | 7.57 | % |
| Required by $C_{23}H_{48}N_2$ | 78.34 | 13.72 | 7.94 | % |

EXAMPLE 71

A mixture of 40 parts by volume of acrylonitrile and 9.2 parts by weight of 2(2',2',6',6'-tetramethylpiperidinyl-4') ethylamine was heated at reflux for 18 hours. The solution was then distilled to give 8 parts by weight (67% of theory yield) of N-(2'''-cyanoethyl)-2[(2',2',-6',6'-tetramethylpiperidinyl-4')ethylamine], boiling at 128°–30°C./0.6mm Hg. and having the following elemental analysis by weight:

|  | C | H | N |  |
| --- | --- | --- | --- | --- |
| Found | 70.80 | 11.37 | 17.50 | % |
| Required by $C_{14}H_{27}N_3$ | 70.83 | 11.46 | 17.70 | % |

I claim:
1. A compound of the formula

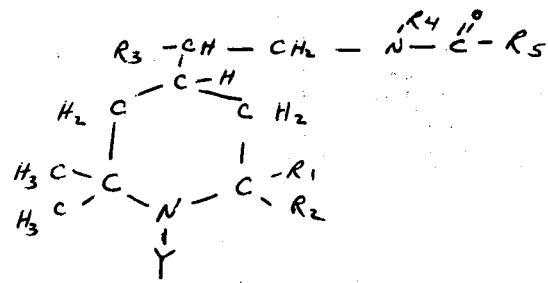

2. A compound of the formula

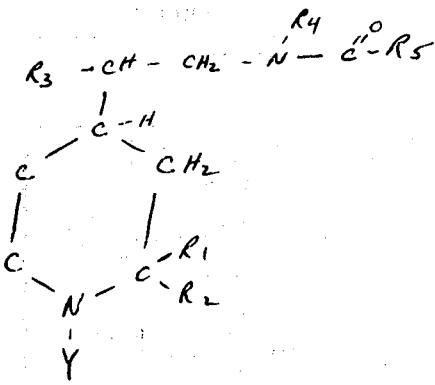

3. A compound according to claim 1 wherein Y is hydrogen or methyl.

4. A compound according to claim 1 wherein $R_1$ and $R_2$ are each methyl.

5. A compound according to claim 1 wherein $R_3$ is hydrogen.

6. A compound according to claim 1 wherein $R_4$ is hydrogen or an alkyl substituent having from 1 to 8 carbon atoms.

7. A compound according to claim 1 which is N-(n-octanoyl)-2-(2',2',6',6'-tetramethylpiperidinyl-4')-ethylamine.

8. A compound according to claim 1 which is N-acetyl-2-(2',2',6',6'-tetramethylpiperidinyl-4')-ethylamine.

* * * * *